(12) United States Patent
Jiwani et al.

(10) Patent No.: US 11,501,401 B2
(45) Date of Patent: Nov. 15, 2022

(54) ALLOCATION OF VEHICLES USING FITNESS INFORMATION

(71) Applicant: ANI TECHNOLOGIES PRIVATE LIMITED, Bengaluru (IN)

(72) Inventors: Moiaz Jiwani, Bilaspur (IN); Azimul Mannan, Bengaluru (IN)

(73) Assignee: ANI TECHNOLOGIES PRIVATE LIMITED, Bengaluru (IN)

( * ) Notice: Subject to any disclaimer, the term of this patent is extended or adjusted under 35 U.S.C. 154(b) by 0 days.

(21) Appl. No.: 16/535,646

(22) Filed: Aug. 8, 2019

(65) Prior Publication Data
US 2020/0279345 A1  Sep. 3, 2020

(30) Foreign Application Priority Data
Mar. 2, 2019  (IN) .............................. 201941008263

(51) Int. Cl.
| G06Q 50/00 | (2012.01) |
| G06Q 10/00 | (2012.01) |
| G06Q 50/30 | (2012.01) |
| G06Q 10/06 | (2012.01) |

(52) U.S. Cl.
CPC ..... G06Q 50/30 (2013.01); G06Q 10/063112 (2013.01)

(58) Field of Classification Search
CPC ........................ G06Q 50/30; G06Q 10/063112
See application file for complete search history.

(56) References Cited

U.S. PATENT DOCUMENTS

| 6,870,478 B2 | 3/2005 | Yasushi et al. |
| 9,183,176 B2 | 11/2015 | Lee et al. |
| 9,605,970 B1 | 3/2017 | Day et al. |
| 10,762,441 B2 * | 9/2020 | O'Herlihy .............. G06N 20/00 |
| 2016/0012445 A1 * | 1/2016 | Villa-Real ............ G06Q 20/353 705/44 |
| 2016/0318468 A1 | 11/2016 | Ricci |
| 2016/0321566 A1 | 11/2016 | Liu et al. |
| 2016/0332535 A1 * | 11/2016 | Bradley ................ B60N 2/002 |
| 2018/0157984 A1 * | 6/2018 | O'Herlihy .............. G06N 20/00 |
| 2019/0061619 A1 * | 2/2019 | Reymann ............. G05D 1/0212 |
| 2019/0130663 A1 * | 5/2019 | Li ....................... G06Q 30/0278 |

(Continued)

FOREIGN PATENT DOCUMENTS

| JP | 2004242945 A | 9/2004 |
| JP | 2005056194 A | 3/2005 |
| JP | 2007047196 A | 2/2007 |

*Primary Examiner* — Hafiz A Kassim
*Assistant Examiner* — Matheus Ribeiro Stivaletti
(74) *Attorney, Agent, or Firm* — Chip Law Group

(57) ABSTRACT

Allocation of a vehicle to a passenger includes receiving a ride request for a ride from a passenger device of a passenger. A ride eligibility of the passenger is determined based on health conditions of the passenger. Further, a set of drivers available for offering the ride are identified. A subset of drivers eligible for offering the ride are selected from the set of drivers based on at least the ride request and health conditions of each driver. A first driver is selected from the subset of drivers and a route is selected from a set of routes, based on the health conditions of the passenger and each driver of the subset of drivers, route conditions of each route, and the ride request. A vehicle associated with the first driver is allocated to the passenger for the ride.

20 Claims, 12 Drawing Sheets

(56) References Cited

U.S. PATENT DOCUMENTS

| | | | |
|---|---|---|---|
| 2019/0204106 A1* | 7/2019 | Lee | G01C 21/367 |
| 2019/0357834 A1* | 11/2019 | Aarts | G08B 21/06 |
| 2019/0360832 A1* | 11/2019 | Emory | G01C 21/3407 |
| 2019/0383621 A1* | 12/2019 | Isaacs | G01C 21/3484 |
| 2020/0101976 A1* | 4/2020 | Celia | G07C 5/0816 |
| 2020/0209850 A1* | 7/2020 | Abu Elreich | G06K 9/00885 |
| 2020/0211042 A1* | 7/2020 | Boladian | G06Q 30/08 |
| 2020/0219337 A1* | 7/2020 | Kwak | G07C 5/0841 |
| 2020/0225051 A1* | 7/2020 | Dhullipala Chenchu | G01C 21/3461 |

* cited by examiner

| PHYSIOLOGICAL PARAMETER ← 306a | SEVERITY CONDITION ← 306b | SEVERITY RATING ← 306c |
|---|---|---|
| BODY TEMPERATURE ← 308a | CRITICAL | 0.9 |
| | HIGH | 0.7 |
| ARRHYTHMIA ← 308b | CRITICAL | 0.9 |
| ASTHMA ← 308c | MILD | 0.5 |

TABLE A

FIG. 3B

| PHYSIOLOGICAL PARAMETER | SEVERITY CONDITION | SEVERITY RATING |
|---|---|---|
| BODY TEMPERATURE | CRITICAL | 0.9 |
| DIABETES | HIGH | 0.7 |
| FLU | CRITICAL | 0.9 |
|  | MILD | 0.5 |
| FATIGUE | CRITICAL | 0.9 |
|  | MILD | 0.5 |

TABLE B

FIG. 3D

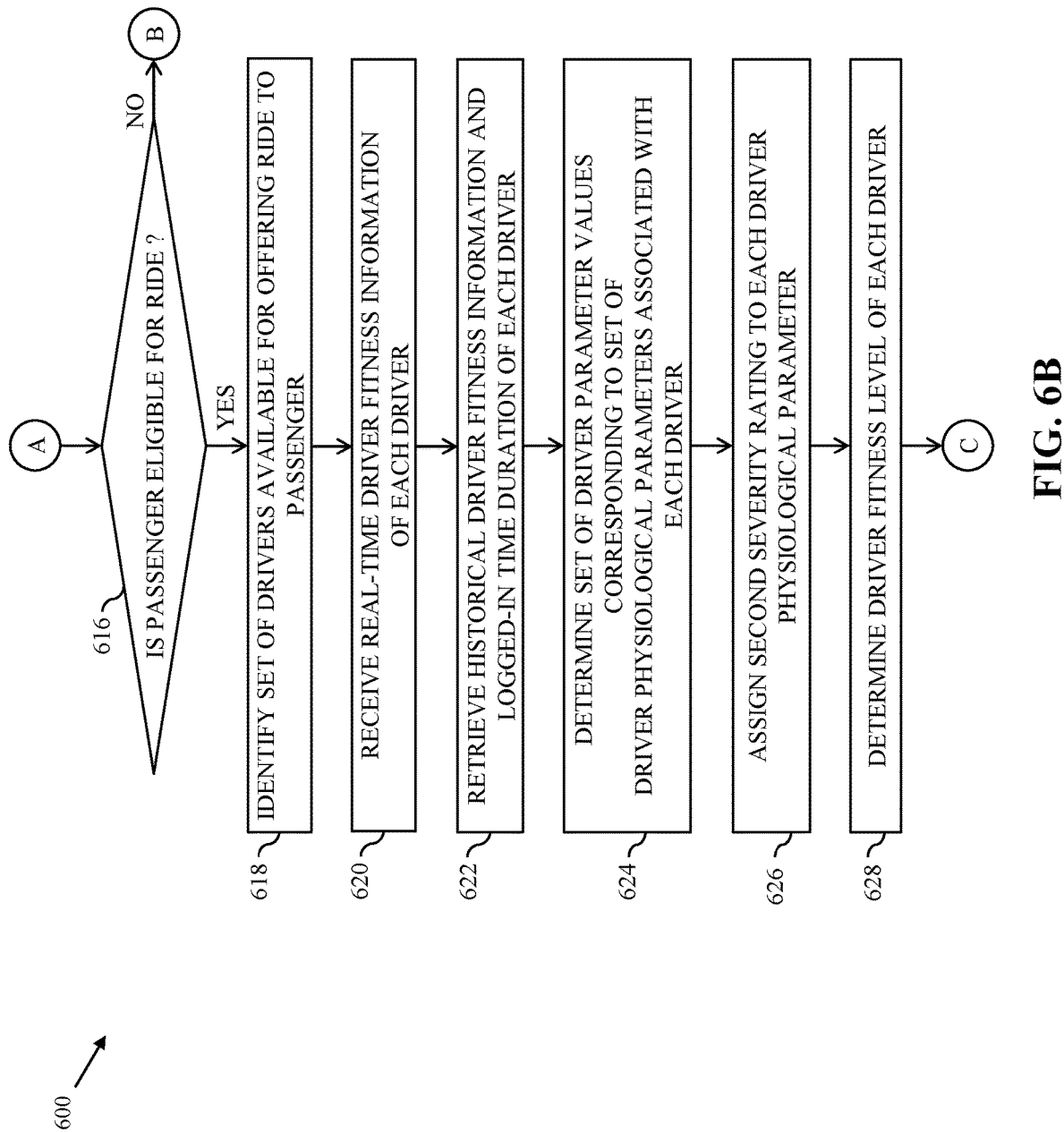

ALLOCATION OF VEHICLES USING FITNESS INFORMATION

CROSS-RELATED APPLICATIONS

This application claims priority of Indian Application Serial No. 201941008263, filed Mar. 2, 2019, the contents of which are incorporated herein by reference.

FIELD

Various embodiments of the disclosure relate generally to vehicle allocation systems. More specifically, various embodiments of the disclosure relate to allocation of vehicles using fitness information.

BACKGROUND

Traveling is an important part of everyone's life. With the advent of the Internet, online booking for on-demand vehicle services has increased enormously. Conventionally, a passenger initiates a ride request for a ride in an online manner by utilizing a ride-haling application that communicates with a ride-haling server associated with a vehicle service provider. The ride-haling server receives the ride request, selects an available driver, and allocates an available vehicle associated with the available driver to the passenger for the ride.

Generally, the selection of the available driver and the subsequent allocation of the available vehicle to the passenger are based on information associated with the ride request such as a source location, a destination location, a ride type, a ride time, a distance between the source and destination locations, or the like. Such traditional ways of selecting the available driver and allocating the available vehicle to the passenger have many disadvantages that may hamper the passenger's and driver's experiences, affect demand and supply, and deteriorate company's brand. For example, with the traditional ways of selection and allocation, there is no surety of completion of the ride by the driver. Further, there might be high chances of accidents. Further, a route being followed by the driver to complete the ride might not be suitable for the driver as well as the passenger.

In light of the foregoing, there exists a need for a technical and reliable solution that overcomes the above-mentioned problems, challenges, and short-comings, and manages selection and allocation of available drivers and vehicles to passengers in a manner that may offer best experiences to the passengers and the drivers, maximize demand and supply, and enhance the company's brand.

SUMMARY

Allocation of vehicles using fitness information of passengers and/or drivers is provided substantially as shown in, and described in connection with, at least one of the figures, as set forth more completely in the claims.

These and other features and advantages of the present disclosure may be appreciated from a review of the following detailed description of the present disclosure, along with the accompanying figures in which like reference numerals refer to like parts throughout.

BRIEF DESCRIPTION OF THE DRAWINGS

FIG. 3B is a tabular diagram that illustrates a set of passenger physiological parameters and a respective first severity rating, in accordance with an exemplary embodiment of the disclosure;

FIG. 3D is a tabular diagram that illustrates a set of driver physiological parameters and a respective second severity rating, in accordance with an exemplary embodiment of the disclosure;

FIGS. 6A-6C, collectively, illustrate a flow chart of a method for allocating the vehicle to the passenger, in accordance with an exemplary embodiment of the disclosure.

DETAILED DESCRIPTION

Figure 1:
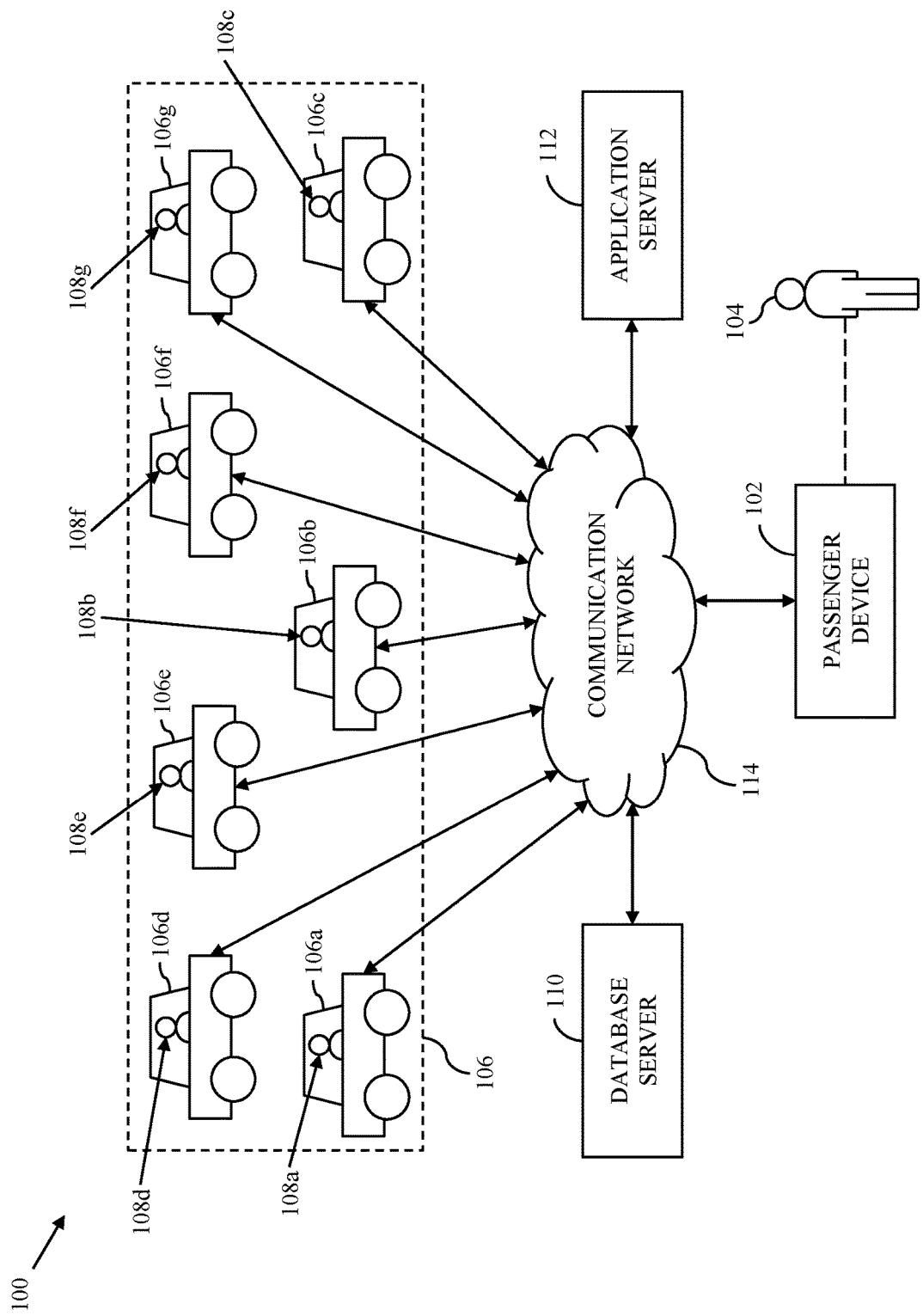
FIG. 1 is a block diagram that illustrates an environment for vehicle allocation, in accordance with an exemplary embodiment of the disclosure.

Certain embodiments of the disclosure may be found in a disclosed apparatus for vehicle allocation. Exemplary aspects of the disclosure provide a method and a system for allocating vehicles using fitness information. The method includes one or more operations that are executed by circuitry of an application server for allocating the vehicles to passengers in the online manner. The circuitry may be configured to receive a ride request for a ride from a passenger device via a communication network. The ride request may include at least one of a source location, a destination location, a vehicle type, or a ride type. The circuitry may be further configured to determine one or more passenger parameter values corresponding to one or more passenger physiological parameters associated with a passenger. The one or more passenger parameter values may be determined based on passenger fitness information of the passenger. The passenger fitness information may include at least one of historical and real-time passenger fitness information of the passenger. The historical passenger fitness information may be retrieved from at least a database server, and include at least historical passenger health data and driver feedback data associated with the passenger. The real-time passenger fitness information may be received from one or more fitness accessories and applications associated with the passenger.

The circuitry may be further configured to assign a first severity rating to each passenger physiological parameter based on a degree of severity associated with each passenger parameter value. The circuitry may be further configured to determine a passenger fitness level of the passenger based on at least one of a passenger parameter value and the first severity rating associated with each of the one or more passenger physiological parameters. The circuitry may be further configured to determine eligibility of the passenger for the ride based on the ride request and the passenger fitness information. For example, the eligibility of the passenger for the ride may be determined based on the ride request and at least one of the passenger fitness level and the one or more passenger parameter values.

Based on the eligibility of the passenger for the ride, the circuitry may be configured to identify a set of drivers available for offering the ride to the passenger. The set of drivers may be identified based on at least the ride request. Upon identification of the set of drivers, the circuitry may be configured to determine, for each driver, one or more driver parameter values of one or more driver physiological parameters. The one or more driver parameter values may be determined based on driver fitness information and a logged-in time duration associated with each driver of the set of drivers. The driver fitness information of each driver may include historical and real-time driver fitness information of each driver. The historical driver fitness information may be retrieved from at least the database server, and include at least historical driver health data and passenger feedback data. The real-time driver fitness information of each driver may be received from one or more fitness accessories and applications associated with each driver. The real-time driver fitness information of each driver may be further received from one or more fitness-monitoring devices installed in each driver's vehicle. The one or more fitness-monitoring devices may include at least an audio-recording device, an image-capturing device, an air quality detector, and an on-board diagnostic sensor (OBD). The real-time driver fitness information may indicate at least real-time driving patterns and real-time health conditions of each driver.

The circuitry may be configured to assign a second severity rating to each driver physiological parameter based on a degree of severity associated with each driver parameter value. The circuitry may be further configured to determine a driver fitness level of each driver based on at least one of the driver parameter value and the second severity rating associated with each of the one or more driver physiological parameters. The circuitry may be further configured to select, from the set of drivers, a subset of drivers based on at least the ride request, the driver fitness information of each driver, the logged-in time duration of each driver, and a count of rides with unfit passengers completed by each driver during a predefined time duration. The eligibility of each driver of the subset of drivers may be determined based on at least one of the driver fitness level and the one or more driver parameter values.

Upon selection of the subset of drivers, the circuitry may be configured to select a first driver from the subset of drivers and a route from a set of routes associated with the ride request. The circuitry may select the first driver and the route based on at least one of the passenger fitness information, the driver fitness information, the logged-in time duration, the ride request, or route information associated with each route. For example, the first driver and the route may be selected based on at least one of the one or more passenger parameter values, the passenger fitness level, the one or more driver parameter values, the driver fitness level, the logged-in time duration, the route information, or the ride request. The route information may include at least one of weather, road, pollution, geographical, or traffic conditions associated with each route. The first driver may be further selected from the subset of drivers based on historical allocation information associated with the passenger and/or each driver of the subset of drivers. The circuitry may be further configured to allocate a first vehicle associated with the first driver to the passenger for the ride.

Various vehicle allocation methods and systems of the disclosure facilitate allocation of a vehicle to a passenger based on real-time and historical fitness information of the passenger and a set of drivers who are available for offering the ride to the passenger. Such allocation ensures that a driver is selected from the set of drivers only when the driver is fit for completing the ride. An unhealthy driver may not be considered for allocation and may be advised to take rest. In one example, when a logged-in time duration of a driver is greater than a threshold value (e.g., 8-10 hours working), the driver may not be considered for long rides such as an outstation ride. The allocation of the vehicle is further based on historical allocation information of the passenger or each driver of the subset of drivers. This ensures that unhealthy drivers are not repeatedly selected to offer ride to unhealthy passengers, or vice-versa. Also, the disclosed vehicle allocation methods and systems ensure that routes for various rides are selected based on the fitness information of the passenger and the set of drivers. Thus, the disclosed methods and the systems facilitate an efficient, effective, and comprehensive way of allocating an available vehicle to a passenger.

FIG. 1 is a block diagram that illustrates an environment 100 for vehicle allocation, in accordance with an exemplary embodiment of the disclosure. The environment 100 includes a passenger device 102 of a passenger 104, a set of vehicles 106 such as vehicles 106a-106g associated with drivers 108a-108g, respectively, a database server 110, an application server 112, and a communication network 114. In an embodiment, the passenger device 102, the set of vehicles 106, the database server 110, and the application server 112 are communicatively coupled to each other via the communication network 114.

The passenger device 102 may include suitable logic, circuitry, interfaces, and/or code, executable by the circuitry, that may be configured to perform one or more operations for online vehicle booking. The passenger device 102 may be a computing device that is utilized, by the passenger 104, to initiate the one or more operations by using a service application (associated with a vehicle service provider such as OLA) running on the passenger device 102. For example, the passenger device 102 may be utilized, by the passenger 104, to provide an input to initiate a ride request for a ride. Various modes of input that can be utilized, by the passenger 104, to initiate the ride request may include, but are not limited to, a touch-based input, a text-based input, a voice-based input, a gesture-based input, or any combination thereof. The passenger device 102 may be further utilized, by the passenger 104, to input ride details for the ride, such as a source location, a destination location, a vehicle type, a ride type, or the like. Upon allocation of an available vehicle to the passenger 104 by the application server 112, the passenger device 102 may be configured to receive allocation information from the application server 112 via the communication network 114. The passenger device 102 may be further utilized, by the passenger 104, to view allocation information including at least one of driver information, vehicle information, or ride information. In an embodiment, the passenger device 102 may be configured to monitor real-time health conditions of the passenger 104 by using a first set of fitness applications that are running on the passenger device 102. In an embodiment, the passenger device 102 may be further configured to monitor the real-time health conditions of the passenger 104 by using a first set of fitness sensors that are integrated within the passenger device 102. Examples of the passenger device 102 may include, but are not limited to, a personal computer, a laptop, a smartphone, and a tablet computer.

The passenger 104 is an individual who wants to avail a vehicle service for the ride by initiating the ride request in an online manner, as described above. The passenger 104 may possess a first set of fitness accessories that monitors, measures, and records real-time fitness information (i.e., the real-time health conditions) of the passenger 104. The first set of fitness accessories may include a first fitness band (shown in FIG. 3A), a first fitness watch (shown in FIG. 3A), and the like. The real-time fitness information of the passenger 104 may also be monitored by way of the first set of fitness applications (shown in FIG. 3A) that are running on the passenger device 102. In an embodiment, the first fitness band, the first fitness watch, and the first set of fitness applications may be configured to generate first, second, and third passenger health monitoring data, respectively. The first, second, and third passenger health monitoring data may include heart rate data, blood pressure data, body temperature data, pulse rate data, sleep data, steps count data, or the like.

A vehicle (such as the vehicle 106a, 106b, 106c, 106d, 106e, 106f, or 106g) is a mode of transport that is deployed by the vehicle service provider to offer the on-demand vehicle services to the passengers such as the passenger 104. Examples of the vehicle may include, but are not limited to, an automobile, a bus, a car, an auto-rickshaw, and a bike. In one example, the vehicle is the micro-type vehicle such as a compact hatchback vehicle. In another example, the vehicle is the mini-type vehicle such as a regular hatchback vehicle. In another example, the vehicle is the prime-type vehicle such as a prime sedan vehicle, a prime play vehicle, a prime sport utility vehicle (SUV), or a prime executive vehicle. In another example, the vehicle is the lux-type vehicle such as a luxury vehicle.

In an embodiment, the set of vehicles 106 may be located within a defined radial distance of the source location of the passenger 104. In another embodiment, the set of vehicles 106 may be located in a geographical region associated with the source location of the passenger 104. In another embodiment, the set of vehicles 106 may be located in other geographical regions that are adjacent to the geographical region associated with the source location of the passenger 104.

In an embodiment, each vehicle of the set of vehicles 106 may include a vehicle device (not shown). The vehicle device may include suitable logic, circuitry, interfaces, and/or code, executable by the circuitry, that may be configured to perform one or more operations. For example, the vehicle device may be configured to establish communication with the passenger device 102, the database server 110, the application server 112, or any other computing device via the communication network 114. Based on the established communication, the vehicle device may be configured to transmit (or receive) queries, messages, data, and requests to (or from) the passenger device 102, the database server 110, the application server 112, or any other computing device via the communication network 114.

In an embodiment, each vehicle of the set of vehicles 106 may include a set of fitness-monitoring devices or sensors. The set of fitness-monitoring devices may include an audio-recording device (shown in FIG. 2), an image-capturing device (shown in FIG. 2), an air quality detector (shown in FIG. 2), an on-board diagnostic (OBD) sensor (shown in FIG. 2), or the like. The set of fitness-monitoring devices may be installed in each vehicle for monitoring, measuring, and recording real-time fitness information of one or more individuals such as drivers or passengers. In an example, the real-time fitness information may include a measure of real-time health conditions and driving or riding patterns of the one or more individuals. The real-time fitness information may also include a measure of air quality, air conditioning, ventilation, or the like.

The real-time fitness information, for example, the health conditions of each driver (such as the drivers 108a-108g associated with the vehicles 106a-106g, respectively) may also be monitored, measured, and recorded by a second set of fitness accessories associated with each driver and a second set of fitness applications (shown in FIG. 3C) running on a corresponding driver device. The second set of fitness accessories may include a second fitness band (shown in FIG. 2), a second fitness watch (shown in FIG. 2), and the like. In an embodiment, the second fitness band, the second fitness watch, and the second set of fitness applications may be configured to generate first, second, and third driver health monitoring data associated with each driver, respectively. The first, second, and third driver health monitoring data associated with each driver may include heart rate data, blood pressure data, body temperature data, pulse rate data, sleep data, steps count data, or the like.

The database server 110 may include suitable logic, circuitry, interfaces, and/or code, executable by the circuitry, that may be configured to perform one or more operations, such as receiving, storing, processing, and transmitting queries, data, or content. The database server 110 may be a data management and storage computing device that is communicatively coupled to the passenger device 102, the set of vehicles 106, and the application server 112 via the communication network 114. In an exemplary embodiment, the database server 110 may be configured to manage and store historical passenger and driver fitness information of one or more passengers (such as the passenger 104) and one or more drivers (such as the drivers 108a-108g).

The historical passenger fitness information may include historical passenger health data and driver feedback data associated with the passenger 104. The historical passenger health data of the passenger 104 may include health history of the passenger 104 including historical or current health conditions (such as a heart condition or a respiratory condition), historical surgeries, allergies, and the like. The driver feedback data associated with the passenger 104 may include feedback provided by various drivers associated with various historical rides availed by the passenger 104 in the past. The driver feedback data may also include health conditions and behavior of the passenger 104 observed by the various drives during the historical rides.

The historical driver fitness information may include historical driver health data and passenger feedback data associated with the various drivers. For example, the historical driver health data of the driver 108a may include health history including historical or current health conditions (such as a heart condition or a respiratory condition), historical surgeries, allergies, and the like. The passenger feedback data associated with the driver 108a may include feedback provided by the one or more passengers (such as the passenger 104) to the driver 108a associated with various historical rides availed by the one or more passengers in the past. The passenger feedback data may also include health conditions and driving behavior of the driver 108a observed by the one or more passengers during the historical rides.

In an embodiment, the database server 110 may be configured to manage and store log-in information of each driver. The log-in information may include a log-in time, a log-out time, and a logged-in time duration of each driver. The logged-in time duration of each driver may indicate a driving time duration of each driver. The database server 110 may be further configured to manage and store historical allocation information associated with the passenger 104 and the drivers 108a-108g. The historical allocation information of the passenger 104 may include driver information of each driver who was previously assigned to the passenger 104 for offering the historical rides. Similarly, the historical allocation information of each driver may include passenger information of the passenger 104 who was previously assigned to each driver for offering the historical rides. The driver information of each driver may include a driver name, a registered vehicle, a vehicle type, driver health conditions during the various historical rides, or information pertaining to a driver account of each driver associated with the vehicle service provider. Similarly, the passenger information of the passenger 104 may include at least a passenger name, a passenger contact number, passenger health conditions during the various historical rides, or information pertaining to a passenger account of the passenger 104 associated with the vehicle service provider.

In an embodiment, the database server 110 may be configured to manage and store route information of one or more routes associated with one or more geographical regions. The route information may include weather, road, pollution, geographical, and traffic conditions associated with the one or more routes. In an embodiment, the database server 110 may be communicatively coupled to a third-party remote server (not shown) or a weblink associated with various departments, such as a meteorological department, a road department, a traffic department, a pollution department, and the like, for extracting and storing the route information. The weather conditions may be indicative of temperature, intensity of rainfall, hail, snow, wind speed, tornadoes, blizzards, or the like. The road conditions may be indicative of road blockages due to maintenance works, water-loggings, intersections, traffic signs, potholes, a presence of snow on roads, or the like. The geographical conditions may indicative of altitudes of various locations within the various geographical regions.

In an embodiment, the database server 110 may be configured to receive a first query from the application server 112 for retrieving information such as the historical passenger fitness information of the passenger 104. In response to the received first query, the database server 110 may be configured to retrieve and transmit the requested information to the application server 112 via the communication network 114. Further, the database server 110 may be configured to receive a second query from the application server 112 for retrieving information such as the historical driver fitness information of the drivers 108a-108g. In response to the received second query, the database server 110 may be configured to retrieve and transmit the requested information to the application server 112 via the communication network 114. The database server 110 may be further configured to receive a third query from the application server 112 for retrieving information such as logged-in time durations of the drivers 108a-108g. In response to the received third query, the database server 110 may be configured to retrieve and transmit the requested information to the application server 112 via the communication network 114. The database server 110 may be further configured to receive a fourth query from the application server 112 for retrieving information such as the historical allocation information of the passenger 104 and the drivers 108a-108d. In response to the received fourth query, the database server 110 may be configured to retrieve and transmit the requested information to the application server 112 via the communication network 114. The database server 110 may be further configured to receive a fifth query from the application server 112 for retrieving the route information of a set of routes connecting the source and destination locations. In response to the received fifth query, the database server 110 may be configured to retrieve and transmit the requested information to the application server 112 via the communication network 114. Examples of the database server 110 include, but are not limited to, a personal computer, a laptop, or a network of computer systems.

The application server 112 may include suitable logic, circuitry, interfaces, and/or code, executable by the circuitry, that may be configured to perform one or more operations for vehicle allocation. The application server 112 may be a computing device, which may include a software framework, that may be configured to create the application server implementation and perform the various operations associated with the vehicle allocation. The application server 112 may be realized through various web-based technologies, such as, but not limited to, a Java web-framework, a .NET framework, a professional hypertext preprocessor (PHP) framework, a python framework, or any other web-application framework. The application server 112 may also be realized as a machine-learning model that implements any suitable machine-learning techniques, statistical techniques, or probabilistic techniques. Examples of such techniques may include expert systems, fuzzy logic, support vector machines (SVM), Hidden Markov models (HMMs), greedy search algorithms, rule-based systems, Bayesian models (e.g., Bayesian networks), neural networks, decision tree learning methods, other non-linear training techniques, data fusion, utility-based analytical systems, or the like. Examples of the application server 112 may include, but are not limited to, a personal computer, a laptop, or a network of computer systems.

In an embodiment, the application server 112 may be configured to receive the ride request for the ride, and the real-time passenger fitness information from the passenger device 102. The application server 112 may be further configured to retrieve the historical passenger fitness information of the passenger 104. The application server 112 may be further configured to determine a set of passenger parameter values corresponding to a set of passenger physiological parameters (or vital signs) associated with the passenger 104. The application server 112 may be further configured to assign a first severity rating to each passenger physiological parameter. Further, in an embodiment, the application server 112 may be configured to determine a passenger fitness level of the passenger 104 based on at least one of the set of passenger parameter values and the first severity rating associated with each of the set of passenger physiological parameters. The passenger fitness level of the passenger 104 may be indicative of an overall health condition of the passenger 104. The application server 112 may be further configured to determine eligibility of the passenger 104 for the requested ride based on at least the ride request and the passenger fitness information of the passenger 104.

In an embodiment, based on the eligibility of the passenger 104 for the ride, the application server 112 may be configured to identify a set of drivers available for offering the ride to the passenger 104. The set of available drivers may be identified based on at least the ride request initiated by the passenger 104. For example, the set of drivers available for offering the ride to the passenger 104 may include the drivers 108a-108g. In an embodiment, the application server 112 may be further configured to retrieve the real-time driver fitness information of the drivers 108a-108g. In one example, the real-time driver fitness information of the driver 108a may be retrieved from the database server 110. In another example, the real-time driver fitness information may be retrieved from the set of fitness-monitoring devices installed in the vehicle 106a, the second set of fitness accessories (i.e., the second fitness band, the second fitness watch, and the like), and the second set of fitness applications associated with the driver 108a. Further, in an embodiment, the application server 112 may be configured to retrieve the historical driver fitness information and the logged-in time duration of each of the drivers 108a-108g from the database server 110.

In an embodiment, the application server 112 may be configured to determine a set of driver parameter values corresponding to a set of driver physiological parameters (or vital signs) associated with each of the drivers 108a-108g. In an embodiment, the application server 112 may be configured to assign a second severity rating to each driver physiological parameter based on a degree of severity associated with each driver parameter value. The application server 112 may be further configured to determine a driver fitness level of each driver based on at least one of the set of driver parameter values and the second severity rating associated with each driver physiological parameter of the corresponding driver. In an embodiment, the application server 112 may be configured to determine eligibility of each driver for offering the ride to the passenger 104. The application server 112 may be further configured to select, from the set of drivers, a subset of drivers eligible for offering the ride to the passenger 104, based on at least the eligibility of each driver.

In an embodiment, the application server 112 may be further configured to retrieve the historical allocation information of the passenger 104 and the drivers 108a-108d from the database server 110. The application server 112 may be further configured to retrieve the route information of the set of routes associated with the ride request from the database server 110.

In an embodiment, the application server 112 may be further configured to select a first driver (such as the driver 108a) from the subset of drivers (such as the drivers 108a-108d) for offering the ride to the passenger 104. Further, the application server 112 may be configured to select, from the set of routes, a route for transporting the passenger 104 from the source location to the destination location. In an embodiment, the application server 112 may select the driver 108a and the route based on at least one of the passenger fitness information of the passenger 104, the driver fitness information and the logged-in time duration associated with each of the drivers 108a-108d, the route information associated with each route, or the ride request. Upon selection of the driver 108a, the application server 112 may be configured to allocate the vehicle 106a associated with driver 108a to the passenger 104 for the ride.

The communication network 114 may include suitable logic, circuitry, interfaces, and/or code, executable by the circuitry, that may be configured to transmit queries, messages, and requests between various entities, such as the passenger device 102, the vehicles 106a-106g, the database server 110, and/or the application server 112. Examples of the communication network 114 include, but are not limited to, a wireless fidelity (Wi-Fi) network, a light fidelity (Li-Fi) network, a local area network (LAN), a wide area network (WAN), a metropolitan area network (MAN), a satellite network, the Internet, a fiber optic network, a coaxial cable network, an infrared (IR) network, a radio frequency (RF) network, and a combination thereof. Various entities in the environment 100 may be coupled to the communication network 114 in accordance with various wired and wireless communication protocols, such as Transmission Control Protocol and Internet Protocol (TCP/IP), User Datagram Protocol (UDP), Long Term Evolution (LTE) communication protocols, or any combination thereof.

In operation, the application server 112 may be configured to receive the ride request for the ride from the passenger device 102 via the communication network 114. The application server 112 may be further configured to receive the real-time passenger fitness information from the passenger device 102, the first set of fitness accessories (i.e., the first fitness band and the first fitness watch), and/or the first set of fitness applications running on the passenger device 102 via the communication network 114. The application server 112 may be further configured to transmit the first query to the database server 110 to retrieve the historical passenger fitness information of the passenger 104.

The application server 112 may be further configured to determine the set of passenger parameter values corresponding to the set of passenger physiological parameters (or vital signs) associated with the passenger 104. The set of passenger parameter values may be determined based on at least one of the historical and real-time passenger fitness information of the passenger 104. The set of passenger physiological parameters may include, but are not limited to, blood pressure, body temperature, allergies, fatigue, flu, diabetes, arthritis, respiratory conditions such as asthma, heart conditions such as arrhythmia, or the like. For example, the application server 112 may determine a temperature value (i.e., a passenger parameter value) of the body temperature (i.e., a passenger physiological parameter) of the passenger 104 based on the real-time passenger fitness information including the body temperature data of the passenger 104.

The application server 112 may be further configured to assign the first severity rating to each passenger physiological parameter based on the degree of severity associated with each passenger parameter value. For example, if the body temperature value of the passenger 104 is greater than 103 degree Fahrenheit (° F.), then the application server 112 may assign the first severity rating of a critical value (e.g., 0.9).

The application server 112 may be further configured to determine the passenger fitness level of the passenger 104. The passenger fitness level may be determined based on at least one of the set of passenger parameter values and the first severity rating associated with each of the set of passenger physiological parameters. The passenger fitness level of the passenger 104 may be indicative of an overall health condition of the passenger 104. The application server 112 may be further configured to determine the eligibility of the passenger 104 for the requested ride based on at least the ride request and the passenger fitness information of the passenger 104. For example, the eligibility of the passenger 104 for the requested ride may be determined based on the ride request and the passenger fitness level of the passenger 104. In another example, the eligibility of the passenger 104 may be determined based on at least the set of passenger parameter values corresponding to the set of passenger physiological parameters.

Based on the eligibility of the passenger 104 for the ride, the application server 112 may be configured to identify the set of drivers available for offering the ride to the passenger 104. In an exemplary embodiment, the set of available drivers may be identified based on at least the ride request initiated by the passenger 104, when the application server 112 determines that the passenger 104 is eligible (i.e., fit) for the ride. For example, the set of drivers may include the one or more drivers who may be in the vicinity of the passenger 104 (i.e., in the same geographical region or near-by geographical regions) and may be available for accepting the ride request in real-time or near-real time. For example, the set of drivers available for offering the ride to the passenger 104 may include the drivers 108a-108g (hereinafter, collectively referred to as, "the set of available drivers").

The application server 112 may be further configured to retrieve the real-time driver fitness information of the drivers 108a-108g. In one example, the real-time driver fitness information of the driver 108a may be retrieved from the database server 110. In another example, the real-time driver fitness information may be retrieved from the set of fitness-monitoring devices installed in the vehicle 106a, the second set of fitness accessories (i.e., the second fitness band, the second fitness watch, and the like), and the second set of fitness applications running on a driver device (not shown) associated with the driver 108a. In a similar manner, the application server 112 may retrieve the real-time driver fitness information of other drivers 108b-108g. Further, the application server 112 may be configured to transmit the second and third queries to the database server 110 to retrieve the historical driver fitness information and the logged-in time duration of each of the drivers 108a-108g.

The application server 112 may be further configured to determine the set of driver parameter values corresponding to the set of driver physiological parameters (or vital signs) associated with each of the drivers 108a-108g. The set of driver parameter values for each driver may be determined based on at least one of the historical and real-time driver fitness information and the logged-in time duration associated with each driver. The set of driver physiological parameters may include, but are not limited to, blood pressure, body temperature, allergies, fatigue, flu, diabetes, arthritis, respiratory conditions such as asthma, heart conditions such as arrhythmia, or the like. The application server 112 may be further configured to assign the second severity rating to each driver physiological parameter. The second severity rating may be assigned based on the degree of severity associated with each driver parameter value.

The application server 112 may be further configured to determine the driver fitness level of each driver. The driver fitness level of each driver may be determined based on at least one of the set of driver parameter values and the second severity rating associated with each driver physiological parameter of the corresponding driver. Further, the application server 112 may be configured to determine the eligibility of each driver for offering the ride to the passenger 104. Such eligibility may be determined based on at least the ride request, the driver fitness information of each driver, the logged-in time duration of each driver, and a count of rides with unfit passengers completed by each driver during a predefined time duration. In an exemplary embodiment, the eligibility of each driver may be determined based on the ride request and at least one of the driver fitness level and the set of driver parameter values associated with each driver. The application server 112 may be further configured to select, from the set of available drivers such as the drivers 108a-108g, the subset of drivers who may be eligible for offering the ride to the passenger 104. The subset of drivers may be selected based on at least the eligibility of each driver. For the sake of ongoing description, it is assumed that the subset of drivers includes the drivers 108a-108d.

The application server 112 may be further configured to transmit the fourth query to the database server 110 to retrieve the historical allocation information of the passenger 104 and the drivers 108a-108d. The application server 112 may be further configured to transmit the fifth query to the database server 110 to retrieve the route information of the set of routes associated with the ride request including the source and destination locations of the passenger 104.

In an embodiment, the application server 112 may be configured to select the first driver from the drivers 108a-108d for offering the ride to the passenger 104. For the sake of ongoing description, it is assumed that the application server 112 selects the driver 108a as the first driver. Further, the application server 112 may be configured to select, from the set of routes, the route for transporting the passenger 104 from the source location to the destination location. In an embodiment, the application server 112 may select the driver 108a and the route based on at least the passenger fitness information of the passenger 104, the driver fitness information and the logged-in time duration associated with each of the drivers 108a-108d, the route information associated with each route, and the ride request. For example, the driver 108a and the route may be selected based on the passenger fitness level and the set of passenger parameter values of the passenger 104, the driver fitness level and the set of driver parameter values of each driver (i.e., the drivers 108a-108d), the ride request, the route information associated with the set of routes, and the historical allocation information associated with the passenger 104 and/or each of the drivers 108a-108d.

Upon selection of the driver 108a and the route, the application server 112 may be configured to allocate the vehicle 106a associated with driver 108a to the passenger 104 for the ride. Further, the application server 112 may be configured to generate and communicate allocation information to the passenger 104 and the driver 108a. Based on the allocation information, the driver 108a may drive the vehicle 106a from a current location (of the vehicle 106a) to the source location and transport the passenger 104 from the source location to the destination location of the passenger 104. In an embodiment, the driver 108a may utilize a digital map (hosted by the application server 112) to navigate between various locations. Various other operations and advantages of the application server 112 have been described in detail in conjunction with FIGS. 2, 3A-3D, 4, 5, 6A-6C, and 7.

Figure 2:
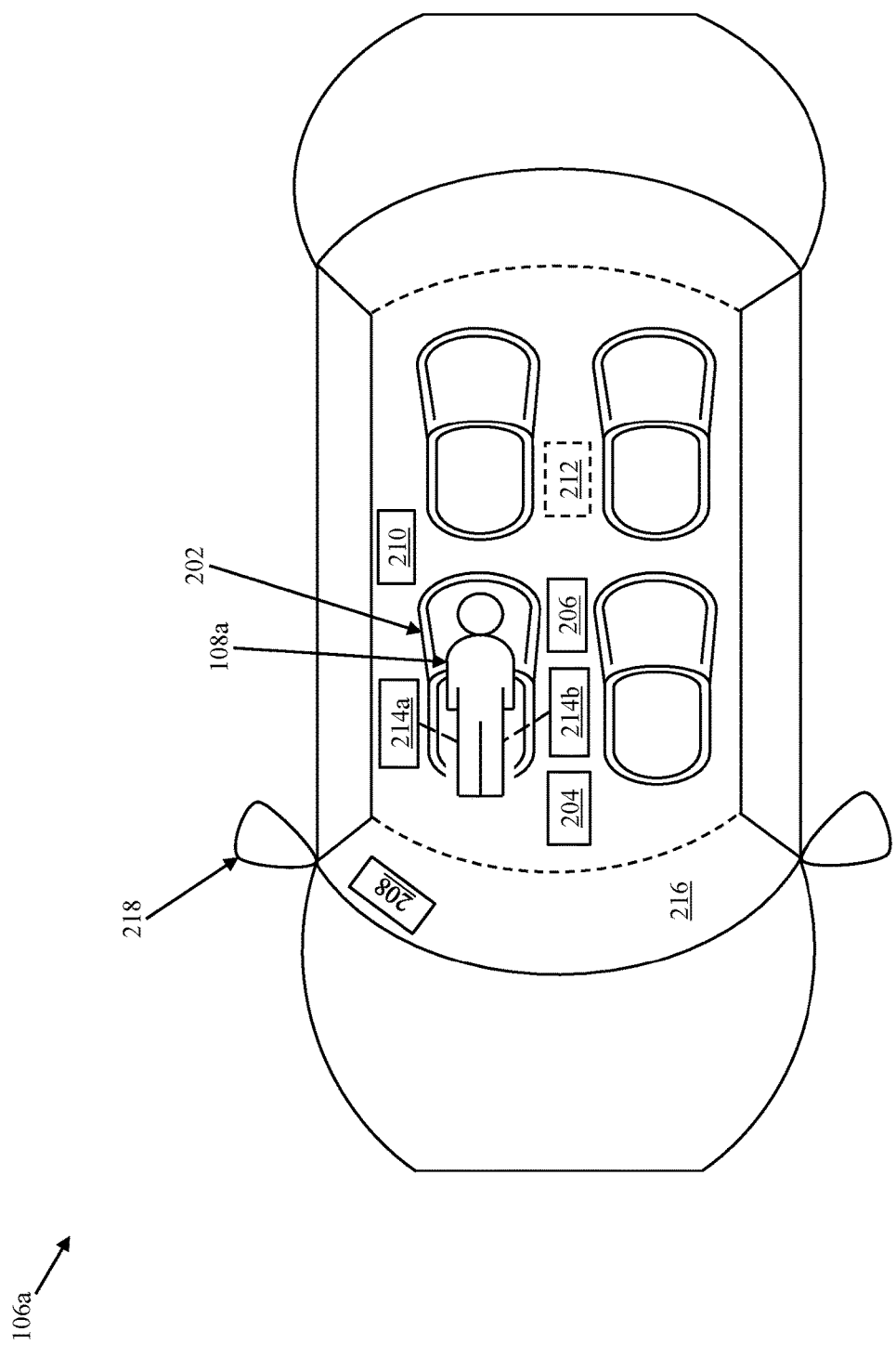
FIG. 2 is a diagram that illustrates a top view of a vehicle of the environment of FIG. 1, in accordance with an exemplary embodiment of the disclosure.

FIG. 2 is a diagram that illustrates a top view of the vehicle 106a, in accordance with an exemplary embodiment of the disclosure. The vehicle 106a includes the driver 108a sitting on a driver seat 202. The vehicle 106a further includes the driver device 204, the audio-recording device 206, the image-capturing device 208, the air quality detector 210, the OBD sensor 212, the second fitness band such as a fitness band 214a, and the second fitness watch such as a fitness watch 214b. The fitness band 214a and the fitness watch 214b are fitness accessories that may be worn by the driver 108a. In an embodiment, the driver device 204, the audio-recording device 206, the image-capturing device 208, the air quality detector 210, the OBD sensor 212, the fitness band 214a, and the fitness watch 214b may be communicatively coupled to each other by a central vehicle device (not shown) of the vehicle 106a. In another embodiment, the driver device 204, the audio-recording device 206, the image-capturing device 208, the air quality detector 210, the OBD sensor 212, the fitness band 214a, and the fitness watch 214b may be communicatively coupled to the database server 110 or the application server 112 via the communication network 114. Also, the central vehicle device of the vehicle 106a may be communicatively coupled to the database server 110 or the application server 112 via the communication network 114.

The driver device 204 may include suitable logic, circuitry, interfaces, and/or code, executable by the circuitry, that may be configured to perform one or more operations. The driver device 204 may be installed with the second set of fitness applications. The second set of fitness applications (running on the driver device 204) may be configured to generate the third driver health monitoring data indicating the real-time health conditions of the driver 108a. The driver device 204 may be configured to transmit the third driver health monitoring data to the database server 110 or the application server 112 for further analysis and processing. Based on the analysis and processing of the third driver health monitoring data, the real-time health conditions of the driver 108a may be determined. The driver device 204 may be utilized, by the driver 108a, to view route information, for example, via a digital map hosted by the application server 112, and follow directions rendered via the digital map to transport the passengers to destination locations. For example, the driver 108a may drive the vehicle 106a to transport the passenger 104 from the source location to the destination location, and during the driving of the vehicle 106s, the driver 108a may utilize the digital map to view and follow the route between the source location and the destination location.

The audio-recording device 206 may include suitable logic, circuitry, interfaces, and/or code, executable by the circuitry, that may be configured to perform one or more operations. The audio-recording device 206 may be installed inside the vehicle 106a for capturing and recording in-vehicle audio (i.e., the real-time audio data) uttered by the driver 108a. The audio-recording device 206 may be configured to capture and record audio data of the driver 108a and transmit the audio data to the application server 112 for further analysis and processing. Based on the analysis and processing of the recorded audio, the real-time health conditions of the driver 108a may be determined. For example, vocal cues, such as tone, pitch, rhythm, rate, and volume retrieved from the audio data, may be analyzed and processed to determine the real-time health conditions of the driver 108a.

The image-capturing device 208 may include suitable logic, circuitry, interfaces, and/or code, executable by the circuitry, that may be configured to perform one or more operations. In an embodiment, the image-capturing device 208 may be a camera device (including one or more image sensors) that is installed inside the vehicle 106a for capturing and recording in-vehicle image and video information (i.e., the real-time image data) associated with various in-vehicle objects of the vehicle 106a that may or may not include the driver 108a. In an embodiment, the image-capturing device 208 may be installed on a windshield 216 of the vehicle 106a. Further, the image-capturing device 208 may be oriented to face inside the vehicle 106a for capturing and recording the real-time image data. In another embodiment, the image-capturing device 208 may be installed on other vehicle parts of the vehicle 106a, such as a side mirror 218, a first door (not shown), or the like, for capturing and recording the real-time image data. Upon recording and capturing of the real-time image data, the image-capturing device 208 may be configured to transmit the real-time image data to the database server 110 or the application server 112 for further analysis and processing. Based on the analysis and processing of the real-time image data, the real-time health conditions of the driver 108a may be determined. For example, the real-time image data may be analyzed and processed to determine whether the driver 108a has an eye infection, diabetes, high blood pressure, jaundice, fatigue, stress, or the like.

The air quality detector 210 may include suitable logic, circuitry, interfaces, and/or code, executable by the circuitry, that may be configured to perform one or more operations. In an exemplary embodiment, the air quality detector 210 may be a sensor that is configured to detect and measure quality of air inside the vehicle 106a, generate the air-quality data, and transmit the air-quality data to the application server 112 for further analysis and processing. Based on the analysis and processing of the air-quality data, real-time in-vehicle conditions (e.g., the quality of air inside the vehicle 106a) may be determined and its effect on health of the driver 108a may also be estimated.

The OBD sensor 212 may include suitable logic, circuitry, interfaces, and/or code, executable by the circuitry, that may be configured to perform one or more operations. In an exemplary embodiment, the OBD sensor 212 may be a sensor (or a group of sensors) that is configured to detect and measure various forms of diagnostic data associated with the vehicle 106a, generate OBD data, and transmit the OBD data to the database server 110 or the application server 112 for further analysis and processing. The OBD data may include data, such as tire pressure, braking frequency, fuel level, temperature, speed, airflow rate, coolant temperature, spark advance, oxygen sensor test results, and the like, associated with the vehicle 106a. Based on the analysis and processing of the OBD data, the real-time driving pattern of the driver 108a may be determined. The real-time driving pattern may be indicative of the real-time health conditions of the driver 108a. For example, an erratic driving pattern, such as sudden brakes and high speed, may indicate that the driver 108a is stressed.

The fitness band 214a and the fitness watch 214b may include suitable logic, circuitry, interfaces, and/or code, executable by the circuitry, that may be configured to perform one or more operations. In an embodiment, the fitness band 214a and the fitness watch 214b are wearable electronic devices that may be worn by the driver 108a. The fitness band 214a and the fitness watch 214b may be configured to monitor the real-time health conditions of the driver 108a and generate the first and second driver health monitoring data indicating the real-time health conditions of the driver 108a, respectively. The fitness band 214a and the fitness watch 214b may be further configured to transmit the first and second driver health monitoring data to the database server 110 or the application server 112 for further analysis and processing. Based on the analysis and processing of the first and second driver health monitoring data, the real-time health conditions of the driver 108a may be determined.

The vehicles 106b-106g may be structurally similar or dissimilar to the vehicle 106a as shown in FIG. 2. However, the installation of various devices or sensors in each of the vehicles 106b-106g and their operations and functionalities may be similar to that of the vehicle 106a as shown and described in conjunction with FIG. 2.

Figure 3A:
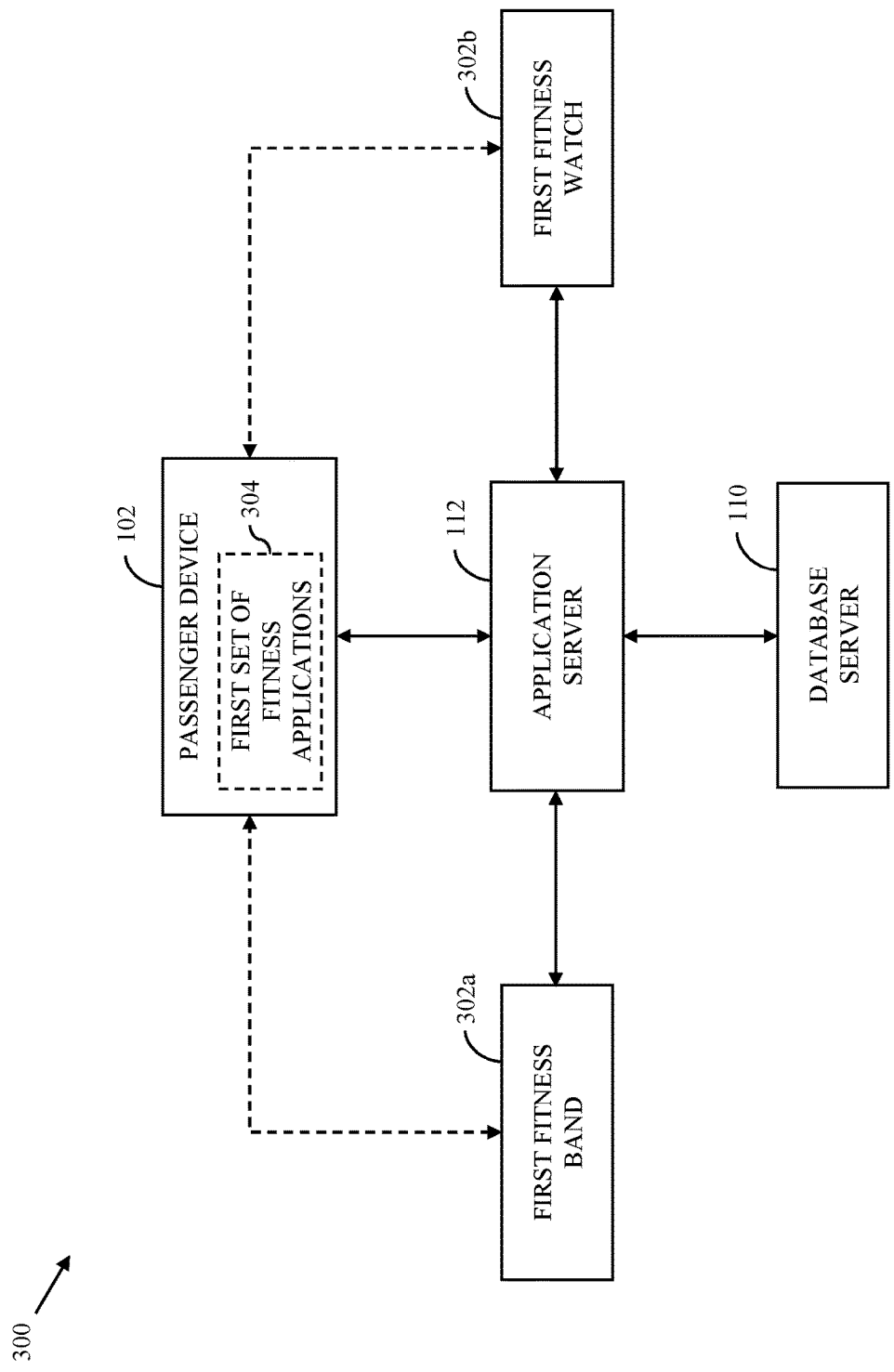
FIG. 3A is a block diagram that illustrates a communication environment, in accordance with an exemplary embodiment of the disclosure.

FIG. 3A is a block diagram that illustrates a communication environment 300 including the application server 112 and various other sources of obtaining the real-time and historical passenger fitness information of the passenger 104, in accordance with an exemplary embodiment of the disclosure. The various other sources may include the first fitness band such as a fitness band 302a, the first fitness watch such as a fitness watch 302b, and the first set of fitness applications such as a set of fitness applications 304 running on the passenger device 102.

The fitness band 302a and the fitness watch 302b may include suitable logic, circuitry, interfaces, and/or code, executable by the circuitry, that may be configured to perform one or more operations. The fitness band 302a and the fitness watch 302b are fitness accessories that are worn by the passenger 104. The fitness band 302a, the fitness watch 302b, and the set of fitness applications 304 may be configured to monitor the real-time health conditions of the passenger 104, and generate the real-time passenger fitness information of the passenger 104 (i.e., at least one of the first, second, and third passenger health monitoring data). The fitness band 302a, the fitness watch 302b, and the passenger device 102 may be communicatively coupled to the database server 110 or the application server 112 via the communication network 114 for transmitting the real-time passenger fitness information of the passenger 104.

The source of the historical passenger fitness information of the passenger 104 is the database server 110. The historical passenger fitness information of the passenger 104 may include the historical passenger health data of the passenger 104 and the driver feedback data associated with the passenger 104. The historical passenger health data may indicate the health history of the passenger 104 and the driver feedback data may indicate the feedback provided by the one or more drivers associated with the historical rides availed by the passenger 104 in the past. The driver feedback data may also indicate the health conditions and behavior of the passenger 104 during the historical rides. The database server 110 may be communicatively coupled to the application server 112 via the communication network 114 for transmitting the historical passenger fitness information of the passenger 104 to the application server 112.

FIG. 3B is a tabular diagram (TABLE A) that illustrates the set of passenger physiological parameters and the respective first severity rating, in accordance with an exemplary embodiment of the disclosure. For example, TABLE A illustrates the set of passenger physiological parameters and the respective first severity rating assigned to each passenger physiological parameter by the application server 112. TABLE A includes columns 306a-306c and rows 308a-308c. The columns 306a-306c represent one or more attributes pertinent to a passenger physiological parameter, a first severity condition, and a first severity rating, respectively.

The rows 308a-308c represent passenger physiological parameters of the passenger 104, such as body temperature, arrhythmia, and asthma, respectively. In an embodiment, the body temperature of the passenger 104 may be determined based on the real-time passenger fitness information received by way of the fitness band 302a, the fitness watch 302b, and the set of fitness applications 304. The severity of the body temperature may be determined based on the temperature value of the body temperature. For example, if the temperature value of the body temperature of the passenger 104 is greater than 103° F., then the body temperature may be classified as a 'critical' severity condition, and accordingly a severity rating of '0.9' may be assigned to the passenger physiological parameter of the body temperature. Similarly, if the temperature value of the body temperature of the passenger 104 is between 100° F. and 103° F., then the body temperature may be classified as a 'high' severity condition, and accordingly a severity rating of '0.7' may be assigned to the passenger physiological parameter of the body temperature.

In an embodiment, information related to the arrhythmia and asthma may be included in the historical passenger health data and may be provided by the passenger 104 at the time of registering with the vehicle service provider. Further, the severity conditions of the arrhythmia and asthma may be provided by the passenger 104 and may be included in the historical passenger health data. For example, the passenger 104 has a 'critical' arrhythmia, and hence a severity rating of '0.9' may be assigned to the passenger physiological parameter of the arrhythmia. Similarly, the passenger 104 has a 'mild' asthma, and hence a severity rating of '0.5' may be assigned to the passenger physiological parameter of the asthma.

Figure 3C:
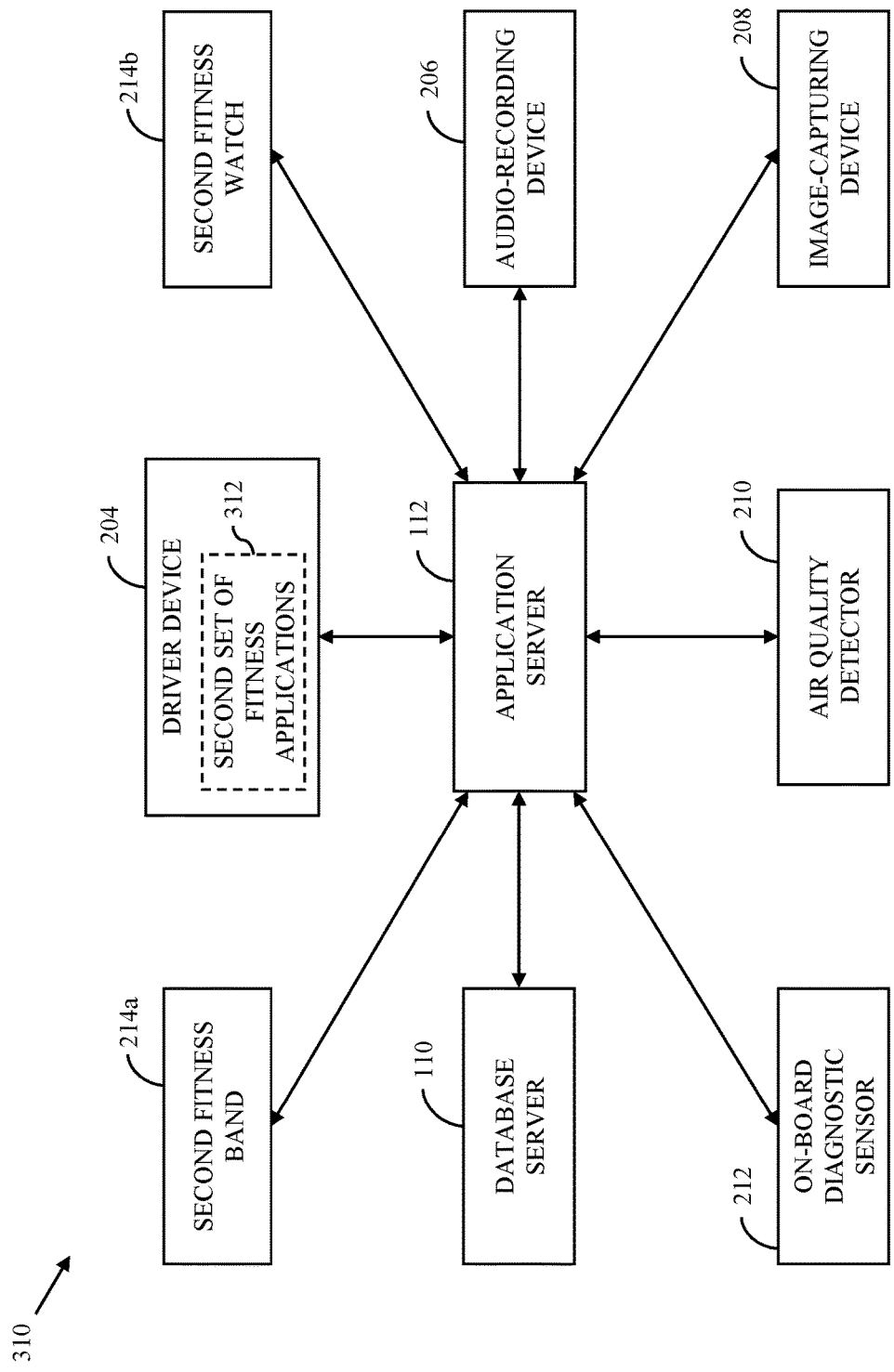
FIG. 3C is a block diagram that illustrates a communication environment, in accordance with an exemplary embodiment of the disclosure.

FIG. 3C is a block diagram that illustrates a communication environment 310 including the application server 112 and various other sources of obtaining the real-time and historical driver fitness information of each driver such as the driver 108a, in accordance with an exemplary embodiment of the disclosure. The various other sources may include the audio-recording device 206, the image-capturing device 208, the air quality detector 210, the OBD sensor 212, the fitness band 214a, the fitness watch 214b, and the second set of fitness applications such as a set of fitness applications 312 running on the driver device 204.

The audio-recording device 206 may be configured to capture and record the in-vehicle audio (i.e., the real-time audio data) of the driver 108a. The real-time audio data may indicate may be analyzed and processed to determine the health conditions of the driver 108a. The image-capturing device 208 may be configured to capture and record the real-time image data. The real-time image data may be analyzed and processed to determine the health conditions of the driver 108a. The air quality detector 210 may be configured to measure the quality of air inside the vehicle 106a, and generate the air-quality data indicating the air quality. The air-quality data may be analyzed and processed to determine the real-time in-vehicle conditions of each vehicle such as the vehicle 106a and the corresponding effect on the health of the driver 108a. The OBD sensor 212 may be configured to generate the OBD data associated with the vehicle 106a. The OBD data may be analyzed and processed to determine the real-time driving pattern of the driver 108a.

The fitness band 214a and the fitness watch 214b are fitness accessories worn by the driver 108a. The fitness band 214a, the fitness watch 214b, and the set of fitness applications 312 may be configured to monitor the real-time health conditions of the driver 108a, and generate the first, second, and third driver health monitoring data, respectively. The fitness band 214a, the fitness watch 214b, and the driver device 204 are communicatively coupled to the application server 112 via the communication network 114 for transmitting the first, second, and third driver health monitoring data, respectively. Thus, the application server 112 may be configured to receive the real-time driver fitness information of the driver 108a from at least one of the audio-recording device 206, the image-capturing device 208, the air quality detector 210, the OBD sensor 212, the fitness band 214a, the fitness watch 214b, or the set of fitness applications 312. At least one of the real-time audio data, the real-time image data, the air-quality data, the OBD data, or the first, second, and third driver health monitoring data may be referred to as the real-time driver fitness information of the driver 108a.

Similarly, the application server 112 may receive the real-time driver fitness information of other drivers 108b-108g from the sets of fitness-monitoring devices installed in the vehicles 106b-106g, the second sets of fitness accessories associated with the drivers 108b-108g, and the second sets of fitness applications running on driver devices of the drivers 108b-108g, respectively.

The source of the historical driver fitness information of the driver 108a is the database server 110. The database server 110 may store the historical driver health data of the driver 108a and the passenger feedback data associated with the driver 108a. The historical driver health data may indicate the health history of the driver 108a and the passenger feedback data may indicate the feedback provided by the one or more passengers associated with the historical rides of the driver 108a. The passenger feedback data may also indicate the health conditions and driving behavior of the driver 108a during the historical rides. The database server 110 may be communicatively coupled to the application server 112 via the communication network 114 for transmitting the historical driver fitness information of the driver 108a to the application server 112. Similarly, the application server 112 may receive the historical driver fitness information of other drivers 108b-108g from the database server 110.

FIG. 3D is a tabular diagram (TABLE B) that illustrates the set of driver physiological parameters and the respective second severity rating, in accordance with an exemplary embodiment of the disclosure. For example, TABLE B illustrates the set of driver physiological parameters and the respective second severity rating assigned to each driver physiological parameter by the application server 112. TABLE B includes columns 314a-314c and rows 316a-316d. The columns 314a-314c represent one or more attributes pertinent to a driver physiological parameter, a second severity condition, and a second severity rating, respectively.

The rows 316a-316d represent driver physiological parameters of the driver 108a, such as body temperature, diabetes, flu, and fatigue respectively. In an embodiment, the body temperature of the driver 108a may be determined based on the real-time driver fitness information received from the fitness band 214a, the fitness watch 214b, and the set of fitness applications 312. The severity of the body temperature may be determined based on the temperature value of the body temperature. For example, if the temperature value of the body temperature of the driver 108a is greater than 103° F., then the body temperature may be classified as a 'critical' severity condition, and accordingly a severity rating of '0.9' may be assigned to the driver physiological parameter of the body temperature. Similarly, if the temperature value of the body temperature of the driver 108a is between 100° F. and 103° F., then the body temperature may be classified as a 'high' severity condition, and accordingly a severity rating of '0.7' may be assigned to the driver physiological parameter of the body temperature.

In an embodiment, information related to the diabetes may be included in the historical driver health data provided by the driver 108a at the time of registering with the vehicle service provider. For example, if the driver 108a has diabetes of a 'critical' severity condition, then a severity rating of '0.9' may be assigned to the driver physiological parameter of the diabetes.

The flu may be detected based on the real-time driver fitness information received from the image-capturing device 208, the fitness band 214a, the fitness watch 214b, and/or the set of fitness applications 312. The severity of the flu may be determined based on the real-time image data and the first, second, and third driver health monitoring data. For example, based on the analysis and processing of the real-time image data and the first, second, and third driver health monitoring data, it is determined that the driver 108a has 'mild' flu and hence a severity rating of '0.5' may be assigned to the driver physiological parameter of the flu.

A fatigue level of the driver 108a may be determined based on the real-time driver fitness information received from the image-capturing device 208, the fitness band 214a, the fitness watch 214b, and/or the set of fitness applications 312. In another embodiment, the fatigue level may also be determined based on the logged-in time duration of the driver 108a. The severity of fatigue may be determined based on the fatigue level. For example, if the logged-in time duration of the driver 108a is greater than 12 hours, or if the driver 108a appears tired, then the fatigue level may be classified as a 'critical' severity condition, and accordingly a severity rating of '0.9' may be assigned to the driver physiological parameter of the fatigue. Similarly, if the logged-in time duration of the driver 108a is between 6-8 hours, or if the driver 108a appears relatively fresh, then the fatigue level may be classified as a 'mild' severity condition, and accordingly a severity rating of '0.5' may be assigned to the driver physiological parameter of the fatigue.

Figure 4:
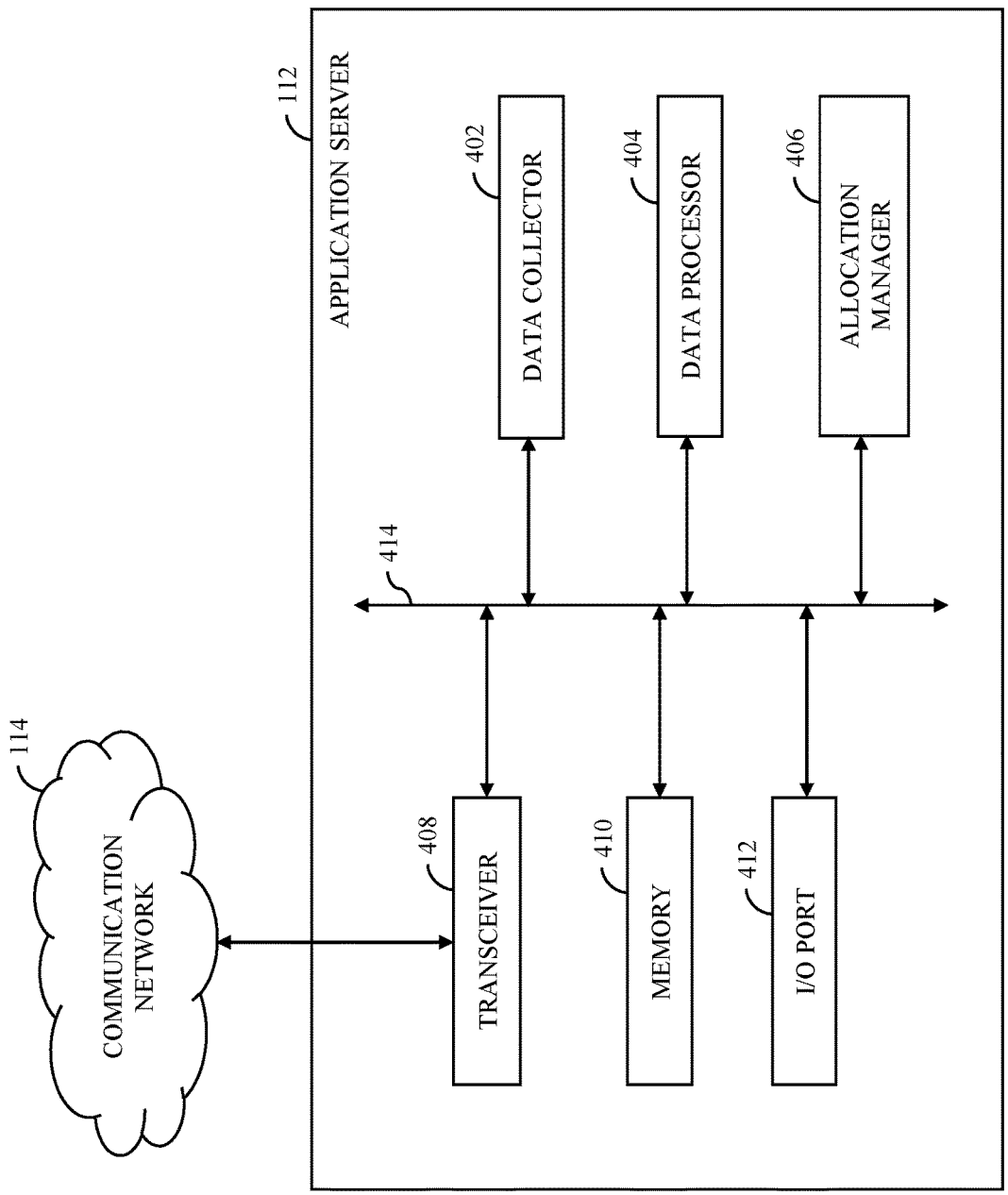
FIG. 4 is a block diagram that illustrates an application server of the environment of FIG. 1, in accordance with an exemplary embodiment of the disclosure.

FIG. 4 is a block diagram that illustrates the application server 112, in accordance with an exemplary embodiment of the disclosure. The application server 112 includes circuitry such as a data collector 402, a data processor 404, an allocation manager 406, a transceiver 408, a memory 410, and an input/output (I/O) port 412 that communicate with each other via a communication bus 414.

The data collector 402 may include suitable logic, circuitry, interfaces, and/or code, executable by the circuitry, that may be configured to perform one or more operations. The data collector 402 may be implemented by one or more processors, such as, but are not limited to, an application-specific integrated circuit (ASIC) processor, a reduced instruction set computing (RISC) processor, a complex instruction set computing (CISC) processor, and a field-programmable gate array (FPGA). The one or more processors may also correspond to central processing units (CPUs), graphics processing units (GPUs), network processing units (NPUs), digital signal processors (DSPs), or the like. In an embodiment, the data collector 402 may include a machine-learning model that implements any suitable machine-learning techniques, statistical techniques, or probabilistic techniques for performing the one or more operations.

In an embodiment, the data collector 402 may be configured to receive the ride request for the ride from the passenger device 102. The data collector 402 may be configured to receive the first, second, and third passenger health monitoring data (i.e., the real-time passenger fitness information) of the passenger 104 from the database server 110, or the fitness band 302a, the fitness watch 302b, and the set of fitness applications 304. The data collector 402 may be configured to transmit the first query to the database server 110 to retrieve the historical passenger fitness information of the passenger 104. The data collector 402 may be further configured to receive the real-time audio data, the real-time image data, the air-quality data, the OBD data, and the first, second, and third driver health monitoring data from the audio-recording device 206, the image-capturing device 208, the air quality detector 210, the OBD sensor 212, the fitness band 214a, the fitness watch 214b, and the set of fitness applications 312, respectively, or the database server 110. Similarly, the data collector 402 may be configured to receive the real-time driver fitness information of each driver such as the drivers 108a-108g. The data collector 402 may be further configured to transmit the second and third queries to the database server 110 to retrieve the historical driver fitness information and the logged-in time duration of the drivers 108a-108g, respectively. The data collector 402 may be further configured to transmit the fourth query to the database server 110 to retrieve the historical allocation information of the passenger 104 and the drivers 108a-108d. The data collector 402 may be further configured to transmit the fifth query to the database server 110 to retrieve the route information associated with the set of routes.

The data processor 404 may include suitable logic, circuitry, interfaces, and/or code, executable by the circuitry, that may be configured to perform one or more operations. Examples of the data processor 404 may include, but are not limited to, an ASIC processor, a RISC processor, a CISC processor, an FPGA processor, a CPU, a GPU, an NPU, and a DSP. It will be apparent to a person of ordinary skill in the art that the data processor 404 may be compatible with multiple operating systems. Further, the data processor 404 may include a machine-learning model that implements any suitable machine-learning techniques, statistical techniques, or probabilistic techniques for performing the one or more operations.

In an embodiment, the data processor 404 may be configured to determine the set of passenger parameter values corresponding to the set of passenger physiological parameters associated with the passenger 104. The set of passenger parameter values may be determined based on at least one of the historical and real-time passenger fitness information of the passenger 104. The data processor 404 may be further configured to assign the first severity rating to each passenger physiological parameter based on the degree of severity associated with each passenger physiological parameter value. The data processor 404 may be further configured to determine the passenger fitness level of the passenger 104 based on at least one of the set of passenger parameter values and the first severity ratings associated with the set of passenger physiological parameters. The data processor 404 may be further configured to determine the eligibility of the passenger 104 for the requested ride. The eligibility of the passenger 104 may be determined based on at least the ride request and at least one of the passenger fitness level and the set of passenger physiological parameter values associated with the passenger 104.

In an embodiment, the data processor 404 may be further configured to determine the set of driver parameter values corresponding to the set of driver physiological parameters for each driver of the set of available drivers. The set of driver parameter values may be determined based on at least one of the historical and real-time driver fitness information and the logged-in time duration of each driver. The data processor 404 may be further configured to assign the second severity rating to each driver physiological parameter based on the degree of severity associated with each driver physiological parameter value. The data processor 404 may be further configured to determine the driver fitness level of each driver based on at least one of the set of driver parameter values and the second severity ratings associated with the set of driver physiological parameters of the corresponding driver.

The allocation manager 406 may include suitable logic, circuitry, interfaces, and/or code, executable by the circuitry, that may be configured to perform one or more allocation operations. The allocation manager 406 may be implemented by one or more processors, such as, but are not limited to, an ASIC processor, a RISC processor, a CISC processor, an FPGA processor, a CPU, a GPU, an NPU, and a DSP. Further, the allocation manager 406 may include a machine-learning model that implements any suitable machine-learning techniques, statistical techniques, or probabilistic techniques for performing the one or more allocation operations.

In an embodiment, the allocation manager 406 may be configured to identify the set of vehicles 106 (such as the vehicles 106a-106g) and the corresponding set of drivers (such as the drivers 108a-108g) available for offering the ride to the passenger 104. The vehicles 106a-106g and the drivers 108a-108g may be identified based on at least the ride request, when the data processor 404 determines that the passenger 104 is eligible for the ride. The allocation manager 406 may be further configured to select, from the set of available drivers such as the drivers 108a-108g, the subset of drivers (such as the drivers 108a-108d) who are eligible for offering the ride. The drivers 108a-108d may be selected based on the ride request and at least one of the driver fitness level and the set of driver physiological parameter values of each driver. The allocation manager 406 may be further configured to select, from the drivers 108a-108d, the driver 108a for offering the ride. The allocation manager 406 may be further configured to select, from the set of routes, the route completing the ride between the source location and destination location of the passenger 104. The driver 108a and the route may be selected based on at least one of the passenger fitness level and the set of passenger physiological parameter values of the passenger 104, the driver fitness level and the set of driver physiological parameter values of each of the drivers 108a-108d, the ride request, the route information associated with the set of routes, and the historical allocation information associated with the passenger 104 and/or the drivers 108a-108d. The allocation manager 406 may be further configured to allocate the vehicle 106a associated with the selected driver 108a to the passenger 104 for the ride.

The transceiver 408 may include suitable logic, circuitry, interfaces, and/or code, executable by the circuitry, that may be configured to transmit (or receive) data to (or from) various servers or devices, such as the passenger device 102, the vehicles 106a-106g, or the database server 110. Examples of the transceiver 408 may include, but are not limited to, an antenna, a radio frequency transceiver, a wireless transceiver, and a Bluetooth transceiver. The transceiver 408 may be configured to communicate with the passenger device 102, the vehicles 106a-106g, or the database server 110 using various wired and wireless communication protocols, such as TCP/IP, UDP, LTE communication protocols, or any combination thereof.

The memory 410 may include suitable logic, circuitry, interfaces, and/or code, executable by the circuitry, that may be configured to store one or more instructions that are executed by the data collector 402, the data processor 404, the allocation manager 406, the transceiver 408, and the I/O port 412 to perform their operations. The memory 410 may be configured to temporarily store various information associated with the passenger 104 and/or the driver 108a-108g. The memory 410 may be further configured to temporarily store the allocation information associated with each vehicle. Examples of the memory 410 may include, but are not limited to, a random-access memory (RAM), a read-only memory (ROM), a programmable ROM (PROM), and an erasable PROM (EPROM).

The I/O port 412 may include suitable logic, circuitry, interfaces, and/or code, executable by the circuitry, that may be configured to perform one or more operations. The I/O port 412 may include various input and output devices that are configured to communicate with the data collector 402, the data processor 404, or the allocation manager 406. Examples of the input devices may include a keyboard, a mouse, a joystick, a touchscreen, a microphone, and the like. Examples of the output devices may include a display screen, a speaker, headphones, and the like.

Figure 5:
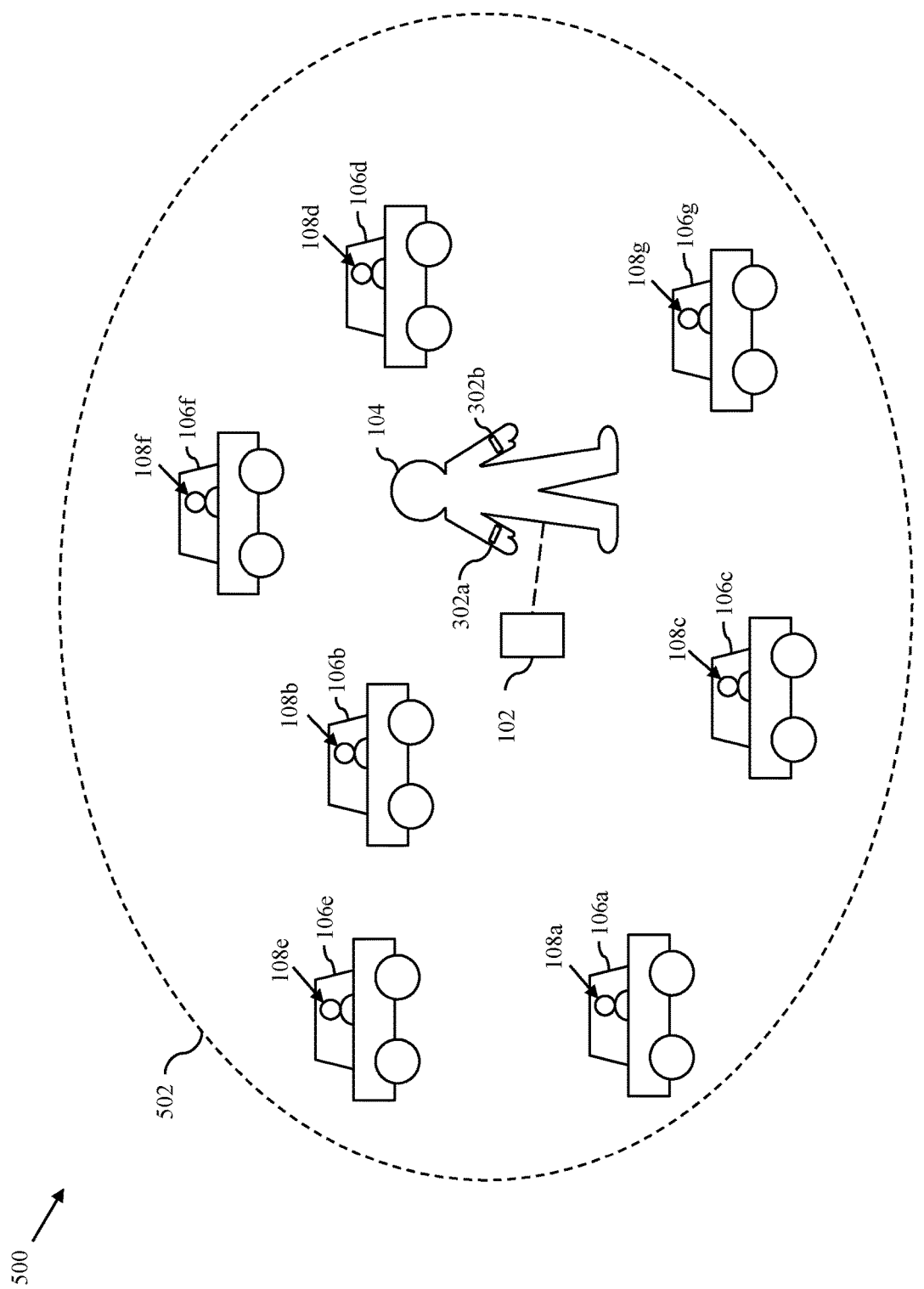
FIG. 5 is a diagram that illustrates an exemplary environment for allocating a vehicle to a passenger, in accordance with an exemplary embodiment of the disclosure.

FIG. 5 is a diagram that illustrates an exemplary environment 500 for allocating the vehicle 106a to the passenger 104, in accordance with an exemplary embodiment of the disclosure. The passenger 104 wants to commute from the source location located in a geographical region 502 to the destination location located in a different geographical region (not shown). The passenger device 102 is utilized, by the passenger 104, to initiate the ride request for the ride. The ride request may include the source location, the destination location, the vehicle type, the ride type, and the like.

The data collector 402 may be configured to receive the ride request from the passenger device 102 via the communication network 114. The data collector 402 may be communicatively coupled to the first set of fitness accessories (such as the fitness band 302a, the fitness watch 302b, and the like) and the set of fitness applications 304 for receiving the real-time passenger fitness information of the passenger 104. The fitness band 302a, the fitness watch 302b, and the set of fitness applications 304 may be configured to monitor the real-time health conditions of the passenger 104 and generate the first, second, and third passenger health monitoring data, respectively. The first, second, and third passenger health monitoring data may include real-time heart activity, blood pressure value, body temperature value, quality of sleep, steps count data, and the like. In an embodiment, at least one of the first, second, and third passenger health monitoring data may be referred to as the real-time passenger fitness information of the passenger 104. The data collector 402 may be further configured to retrieve the historical passenger fitness information of the passenger 104 from the database server 110.

The data processor 404 may be configured to determine the set of passenger parameter values based on at least one of the real-time and historical passenger fitness information. For example, the data processor 404 may determine a blood pressure value (i.e., a passenger parameter value) of the blood pressure (i.e., a passenger physiological parameter) of the passenger 104 based on the real-time passenger fitness information of the passenger 104. Other examples of the passenger physiological parameters may include, but are not limited to, body temperature, allergies, fatigue, flu, diabetes, arthritis, respiratory conditions such as asthma, and heart conditions such as arrhythmia. The data processor 404 may be further configured to assign the first severity rating to each passenger physiological parameter. For example, if the blood pressure value is greater than 180 over 120 mm Hg (millimeter of mercury), then the data processor 404 may assign the first severity rating of a critical value (e.g., 0.9). Further, the data processor 404 may be configured to determine the passenger fitness level of the passenger 104 based on at least one of the passenger parameter value and the first severity rating associated with each passenger physiological parameter. The passenger fitness level of the passenger 104 may be indicative of the overall health condition of the passenger 104. The data processor 404 may be further configured to determine the eligibility of the passenger 104 for the requested ride based on the ride request and at least one of the set of passenger physiological parameter values and the passenger fitness level of the passenger 104.

Based on the eligibility of the passenger 104 for the ride (i.e., when the data processor 404 determines that the passenger 104 is eligible for the ride), the allocation manager 406 may be configured to identify the set of drivers available for offering the ride to the passenger 104 based on at least the ride request. For example, the set of drivers available for offering the ride may include the one or more drivers who are in the vicinity of the passenger 104, for example, in the same geographical region 502. Here, the set of available drivers may correspond to the drivers 108a-108g. The drivers 108a-108g are associated with the vehicles 106a-106g, respectively.

In an embodiment, the data collector 402 may be further configured to receive the real-time driver fitness information of each driver from the second set of fitness accessories (such as the fitness band 214a, the fitness watch 214b, and the like) worn by each driver, the second set of fitness applications (such as the set of fitness applications 312) running on the driver device (such as the driver device 204) of each driver, and the set of fitness-monitoring devices (such as the audio-recording device 206, the image-capturing device 208, the air quality detector 210, the OBD sensor 212, and the like) installed inside each vehicle. The real-time driver fitness information of each driver may include at least one of the real-time audio data, the real-time image data, the air-quality data, the OBD data, or the driver health monitoring data. The data collector 402 may be further configured to retrieve the historical driver fitness information and the logged-in time duration of the drivers 108a-108g.

The data processor 404 may be configured to determine the set of driver parameter values for each driver based on at least one of the real-time and historical driver fitness information and the logged-in time duration of each driver. The data processor 404 may be further configured to assign the second severity rating to each driver physiological parameter based on the degree of severity associated with each driver physiological parameter value. Further, the data processor 404 may be configured to determine the driver fitness level of each driver based on the set of driver parameter values and the second severity ratings associated with the set of driver physiological parameters.

The allocation manager 406 may be configured to select, from the set of available drivers, the subset of drivers who are eligible for offering the ride to the passenger 104. The subset of drivers may be selected based on the ride request and at least one of the driver fitness level and the set of driver physiological parameter values associated with each driver. In the current exemplary scenario, the set of available drivers includes the drivers 108a-108g and the subset of drivers includes the drivers 108a-108d.

The data collector 402 may be further configured to retrieve the historical allocation information of the passenger 104 and each of the drivers 108a-108d. The data collector 402 may be further configured to retrieve the route information of the set of routes connecting the source and destination locations of the passenger 104. The route information may include weather, road, pollution, geographical, and traffic conditions associated with the set of routes. In an embodiment, the data processor 404 may assign a third severity rating to each route based on the route information (i.e., weather, road, pollution, geographical, and traffic conditions) of the set of routes. For example, if weather conditions associated with any of the set of routes are 'critically' severe, then a third severity rating of '0.9' may be assigned to the route.

The allocation manager 406 may be further configured to select the first driver (such as the driver 108a) from the subset of drivers (such as the drivers 108*a*-108*d*) for offering the ride to the passenger 104. The allocation manager 406 may be further configured to select the route from the set of routes. The driver 108*a* and the route may be selected based on at least one of the passenger fitness level and the set of passenger physiological parameter values, the driver fitness level and the set of driver physiological parameter values of each of the drivers 108*a*-108*d*, the third severity rating associated with each route of the set of routes, or the historical allocation information of the passenger 104 and/or each of the drivers 108*a*-108*d*. The allocation manager 406 may be further configured to allocate the vehicle 106*a* associated with the driver 108*a* to the passenger 104 for the ride. Thus, the allocation manager 406 selects and allocates an available driver (such as the driver 108*a*) who is most fit for the ride. Further, the route is selected such that the route conditions along the selected route may not have an adverse effect on the health conditions of the passenger 104 and/or the driver 108*a*.

Figure 6A:
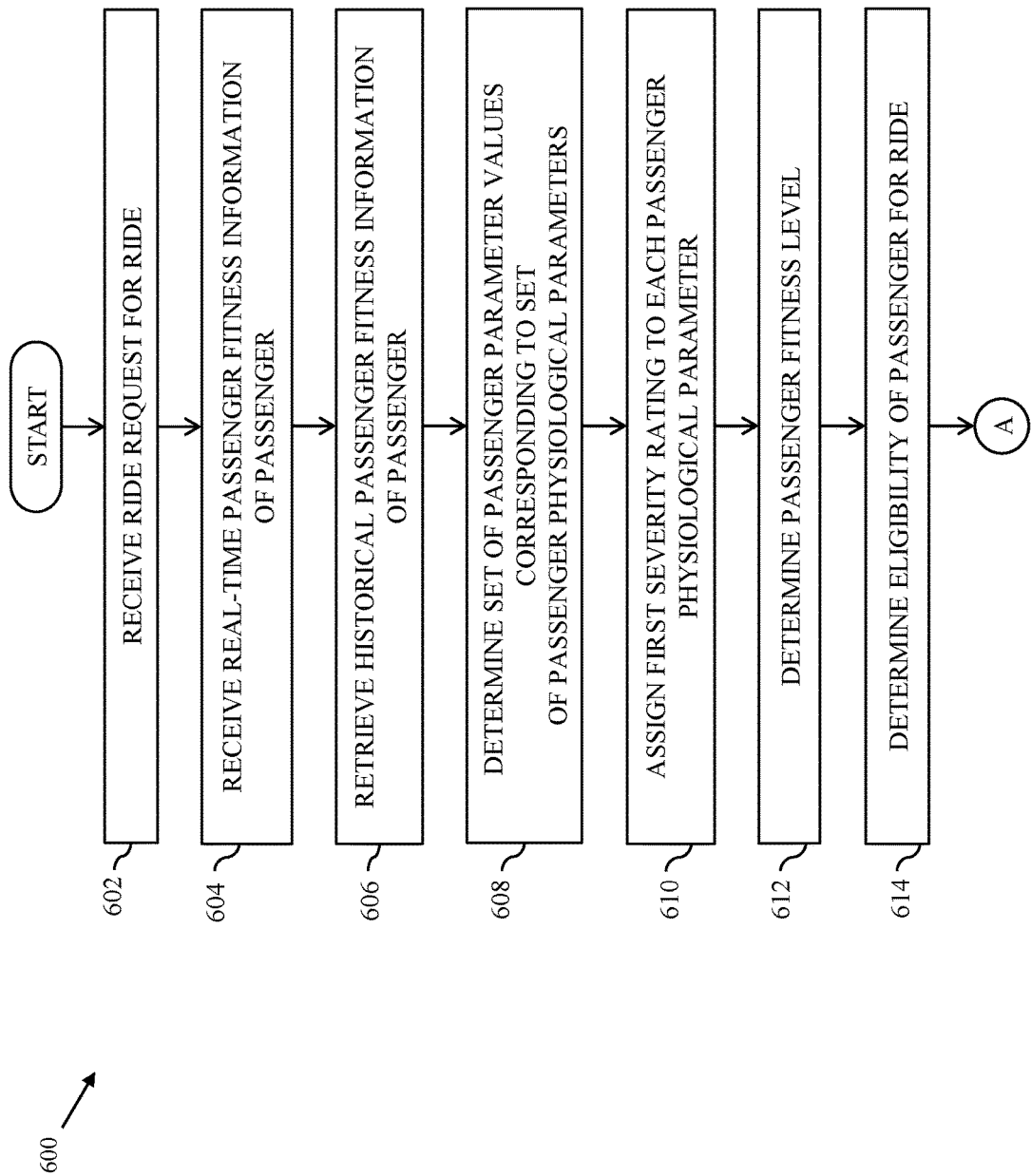
Figure 6C:
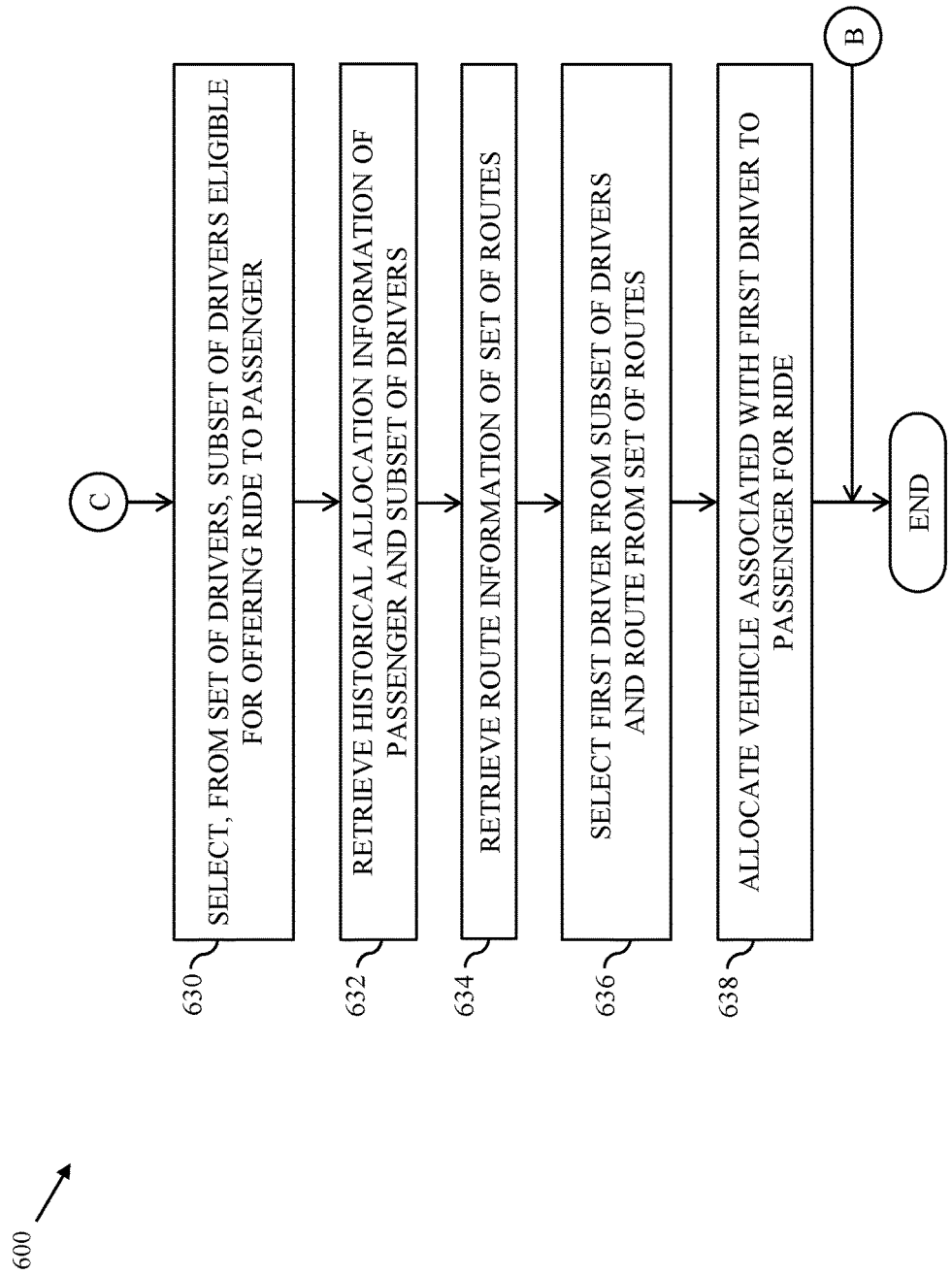

FIGS. 6A-6C, collectively, illustrate a flow chart of a method for allocating the vehicle 106*a* to the passenger 104, in accordance with an exemplary embodiment of the disclosure. At 602, the ride request for the ride is received. In an embodiment, the application server 112 may be configured to receive the ride request from the passenger device 102 via the communication network 114. The ride request may include at least one of the source location, the destination location, the vehicle type, or the ride type.

At 604, the real-time passenger fitness information of the passenger 104 is received. In an embodiment, the application server 112 may be configured to receive the real-time passenger fitness information of the passenger 104 (such as the first, second, and third passenger health monitoring data) from the first set of fitness accessories (such as the fitness band 302*a*, the fitness watch 302*b*, and the like) and the set of fitness applications 304 running on the passenger device 102.

At 606, the historical passenger fitness information of the passenger 104 is retrieved. In an embodiment, the application server 112 may be configured to retrieve the historical passenger fitness information of the passenger 104 from the database server 110. The historical passenger fitness information may indicate at least the health history of the passenger 104 and the health conditions and behavior of the passenger 104 during the historical rides availed by the passenger 104.

At 608, the set of passenger parameter values corresponding to the set of passenger physiological parameters is determined. In an embodiment, the application server 112 may be configured to determine the set of passenger parameter values based on at least one of the real-time and historical passenger fitness information.

At 610, the first severity rating is assigned to each passenger physiological parameter. In an embodiment, the application server 112 may be configured to assign the first severity rating to each passenger physiological parameter based on the degree of severity associated with each passenger physiological parameter value.

At 612, the passenger fitness level is determined. In an embodiment, the application server 112 may be configured to determine the passenger fitness level of the passenger 104 based on at least one of the passenger parameter value and the first severity rating associated with each passenger physiological parameter.

At 614, the eligibility of the passenger 104 for the ride is determined. In an embodiment, the application server 112 may be configured to determine the eligibility of the passenger 104 for the ride based on the ride request, and at least one of the set of passenger physiological parameter values and the passenger fitness level of the passenger 104.

At 616, it is determined whether the passenger 104 is eligible for the ride. If at 616, it is determined that the passenger 104 is eligible for the ride, then 618 is executed. If at 616, it is determined that the passenger 104 is not eligible for the ride, then the process ends.

At 618, the set of drivers available for offering the ride to the passenger 104 is identified. In an embodiment, the application server 112 may be configured to identify the set of available drivers (the drivers 108*a*-108*g*) based on at least the ride request.

At 620, the real-time driver fitness information of each driver is received. In an embodiment, the application server 112 may be configured to receive the real-time driver fitness information of each of the drivers 108*a*-108*g* from the second set of fitness accessories (such as the fitness band 214*a*, the fitness watch 214*b*, and the like) worn by each driver. The real-time driver fitness information of each driver may be further received from the second set of fitness applications (such as the set of fitness applications 312) running on the driver device (such as the driver device 204) of each driver. The real-time driver fitness information of each driver may be further received from the set of fitness-monitoring devices (such as the audio-recording device 206, the image-capturing device 208, the air quality detector 210, the OBD sensor 212, and the like) installed in each vehicle. In an embodiment, the real-time driver fitness information of each driver may include at least one of the real-time audio and image data, the air-quality data, the OBD data, and the first, second, or third driver health monitoring data associated with each driver.

At 622, the historical driver fitness information and the logged-in time duration of each driver are retrieved. In an embodiment, the application server 112 may be configured to retrieve the historical driver fitness information and the logged-in time duration of each driver from the database server 110.

At 624, the set of driver parameter values corresponding to the set of driver physiological parameters associated with each driver is determined. In an embodiment, the application server 112 may be configured to determine the set of driver parameter values based on at least one of the real-time and historical driver fitness information and the logged-in time duration of each driver.

At 626, the second severity rating is assigned to each driver physiological parameter. In an embodiment, the application server 112 may be configured to assign the second severity rating to each driver physiological parameter based on the degree of severity associated with each driver physiological parameter value.

At 628, the driver fitness level of each driver is determined. In an embodiment, the application server 112 may be configured to determine the driver fitness level of each driver based on at least one of the driver parameter value and the second severity rating associated with each driver physiological parameter of the corresponding driver.

At 630, the subset of drivers eligible for offering the ride to the passenger 104 is selected from the set of available drivers. In an embodiment, the application server 112 may be configured to select, from the set of available drivers such as the drivers 108*a*-108*g*, the subset of drivers (such as the drivers 108*a*-108*d*) who are eligible for offering the ride to the passenger 104. The subset of drivers (such as the drivers 108*a*-108*d*) may be selected based on the ride request and at least one of the set of driver physiological parameter values and the driver fitness level of each of the drivers 108a-108g.

At 632, the historical allocation information of the passenger 104 and the subset of drivers (such as the drivers 108a-108d) is retrieved. In an embodiment, the application server 112 may be configured to retrieve the historical allocation information from the database server 110. At 634, the route information associated with the set of routes is retrieved. In an embodiment, the application server 112 may be configured to retrieve the route information associated with the set of routes connecting the source and destination locations of the passenger 104.

At 636, the first driver and the route are selected from the subset of drivers (such as the drivers 108a-108d) and the set of routes. In an embodiment, the application server 112 may be configured to select the first driver (such as the driver 108a) from the subset of drivers (such as the drivers 108a-108d) for offering the ride to the passenger 104. Further, the application server 112 may be configured to select the route from the set of routes to be traversed by the first driver (such as the driver 108a) for completing the ride. The first driver (such as the driver 108a) and the route may be selected based on at least one of the ride request, the passenger fitness level and the set of passenger physiological parameter values of the passenger 104, the driver fitness level and the set of driver physiological parameter values of each of the drivers 108a-108d, the route information of the set of routes, or the historical allocation information of the passenger 104 and/or each of the drivers 108a-108d. At 638, the vehicle 106a associated with the first driver (such as the driver 108a) is allocated to the passenger 104 for the ride. In an embodiment, the application server 112 may be configured to allocate the vehicle 106a associated with the driver 108a to the passenger 104 for the ride.

Figure 7:
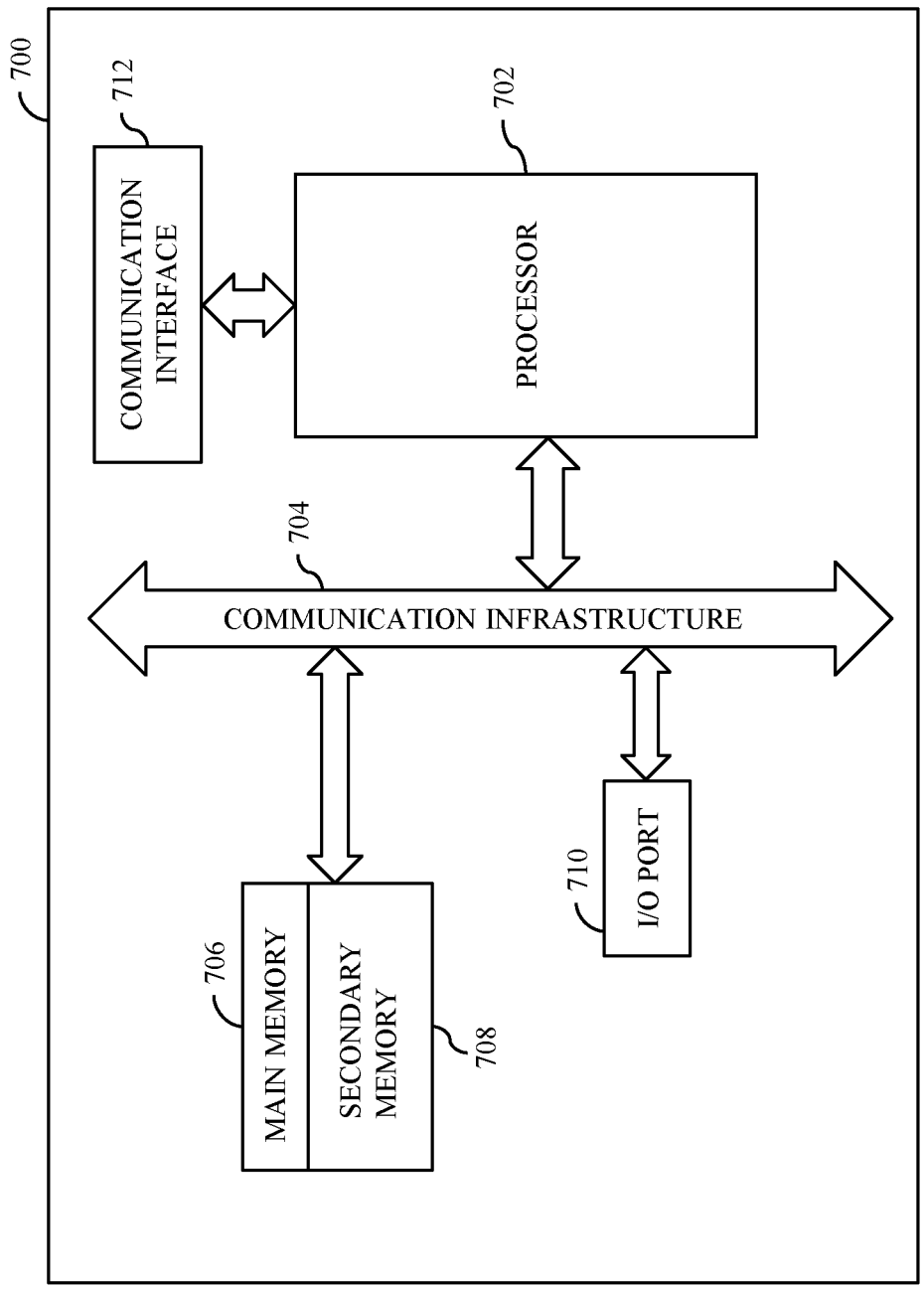
FIG. 7 is a block diagram that illustrates a system architecture of a computer system for allocating the vehicle to the passenger, in accordance with an exemplary embodiment of the disclosure.

FIG. 7 is a block diagram that illustrates a system architecture of a computer system 700 for allocating the vehicle (such as the vehicle 106a) to the passenger 104, in accordance with an exemplary embodiment of the disclosure. An embodiment of the disclosure, or portions thereof, may be implemented as computer readable code on the computer system 700. In one example, the database server 110 and the application server 112 of FIG. 1 may be implemented in the computer system 700 using hardware, software, firmware, non-transitory computer readable media having instructions stored thereon, or a combination thereof and may be implemented in one or more computer systems or other processing systems. Hardware, software, or any combination thereof may embody modules and components used to implement the vehicle allocation methods of FIGS. 6A-6C.

The computer system 700 may include a processor 702 that may be a special purpose or a general-purpose processing device. The processor 702 may be a single processor, multiple processors, or combinations thereof. The processor 702 may have one or more processor "cores." Further, the processor 702 may be coupled to a communication infrastructure 704, such as a bus, a bridge, a message queue, the communication network 114, multi-core message-passing scheme, and the like. The computer system 700 may further include a main memory 706 and a secondary memory 708. Examples of the main memory 706 may include RAM, ROM, and the like. The secondary memory 708 may include a hard disk drive or a removable storage drive (not shown), such as a floppy disk drive, a magnetic tape drive, a compact disc, an optical disk drive, a flash memory, or the like. Further, the removable storage drive may read from and/or write to a removable storage device in a manner known in the art. In an embodiment, the removable storage unit may be a non-transitory computer readable recording media.

The computer system 700 may further include an I/O port 710 and a communication interface 712. The I/O port 710 may include various input and output devices that are configured to communicate with the processor 702. Examples of the input devices may include a keyboard, a mouse, a joystick, a touchscreen, a microphone, and the like. Examples of the output devices may include a display screen, a speaker, headphones, and the like. The communication interface 712 may be configured to allow data to be transferred between the computer system 700 and various devices that are communicatively coupled to the computer system 700. Examples of the communication interface 712 may include a modem, a network interface, i.e., an Ethernet card, a communications port, and the like. Data transferred via the communication interface 712 may be signals, such as electronic, electromagnetic, optical, or other signals as will be apparent to a person of ordinary skill in the art. The signals may travel via a communications channel, such as the communication network 114, which may be configured to transmit the signals to the various devices that are communicatively coupled to the computer system 700. Examples of the communication channel may include a wired, wireless, and/or optical medium such as cable, fiber optics, a phone line, a cellular phone link, a radio frequency link, and the like. The main memory 706 and the secondary memory 708 may refer to non-transitory computer readable mediums that may provide data that enables the computer system 700 to implement the vehicle allocation methods illustrated in FIGS. 6A-6C.

Various embodiments of the disclosure provide the application server 112 for allocating a vehicle to a passenger in an online manner. The application server 112 may be configured to receive, from the passenger device 102 via the communication network 114, the ride request for the ride. Based on at least the ride request and the passenger fitness information of the passenger 104, the application server 112 may be configured to determine the eligibility of the passenger 104 for the ride. Based on the eligibility of the passenger 104 for the ride, the application server 112 may be configured to identify the set of drivers (such as the drivers 108a-108g) available for offering the ride based on at least the ride request. The application server 112 may be further configured to select, from the set of available drivers, the subset of drivers (such as the drivers 108a-108d) who are eligible for offering the ride based on at least the ride request, and the driver fitness information and the logged-in time duration associated with each driver of the set of available drivers. The application server 112 may be further configured to select the first driver (such as the driver 108a) from the subset of drivers and the route from the set of routes associated with the ride request. The first driver and the route may be selected based on at least one of the passenger fitness information, the driver fitness information, the logged-in time duration, the ride request, or the route information associated with each route. The application server 112 may be further configured to allocate the first vehicle (such as the vehicle 106a) associated with the first driver (such as the driver 108a) to the passenger 104 for the ride.

Various embodiments of the disclosure provide a non-transitory computer readable medium having stored thereon, computer executable instructions, which when executed by a computer, cause the computer to execute operations for allocating a vehicle to a passenger in an online manner. The operations include receiving, by the application server 112 from the passenger device 102 via the communication network 114, the ride request for the ride. The operations further include determining, by the application server 112, the eligibility of the passenger 104 for the ride based on at least the passenger fitness information of the passenger 104 and the ride request. The operations further include identifying, by the application server 112, based on the eligibility of the passenger 104 for the ride, the set of drivers (such as the drivers 108a-108g) available for offering the ride based on at least the ride request. The operations further include selecting, by the application server 112, from the set of drivers such as the drivers 108a-108g, the subset of drivers (such as the drivers 108a-108d) who are eligible for offering the ride based on at least the ride request, and the driver fitness information and the logged-in time duration associated with each driver of the set of drivers. The operations further include selecting, by the application server 112, the first driver (such as the driver 108a) from the subset of drivers and the route from the set of routes associated with the ride request. The first driver and the route may be selected based on at least one of the passenger fitness information, the driver fitness information, the logged-in time duration, the ride request, or the route information associated with each route. The operations further include allocating, by the application server 112, the first vehicle (such as the vehicle 106a) associated with the first driver (such as the driver 108a) to the passenger 104 for the ride.

The disclosed embodiments encompass numerous advantages. Specific advantages of the method and the system include allocating a vehicle (such as the vehicle 106a) to a passenger (such as the passenger 104) based on real-time and historical passenger fitness information of the passenger 104 and/or real-time and historical driver fitness information of drivers (such as the drivers 108a-108g) available for offering a ride to the passenger 104. Thus, the method and the system of the disclosure ensure that a driver (such as the driver 108a) from the available drivers is selected for offering the ride to the passenger 104 only if the driver is fit for the ride. Similarly, an unfit driver (e.g., a driver who may not be able to complete a ride or may be likely to be involved in an accident) is not considered for allocation to the passenger 104 and may be advised to take rest or consult a doctor. Further, by using the health conditions of the passenger 104 and the available drivers, the method and the system of the disclosure may allow selecting the driver for offering the ride to the passenger 104 based on a particular health condition of the passenger 104. For example, if the passenger 104 has a heart condition, the driver who is a medical practitioner may be selected for offering the ride to the passenger 104, and may be provided with a set of instructions to handle emergency situations associated with the passenger 104. Further, the method and the system of the disclosure may ensure that, at any time instant, a count of unfit drivers in a geographical region is less than an undesirable number. The allocation of the vehicle is further based on logged-in time durations of the available drivers. Thus, if the driver has a logged-in time duration greater than a threshold value (e.g., a driver has been driving for 8-10 hours), then the driver may not be considered for an outstation ride. Similarly, if a logged-in time duration of the driver is more than 12-14 hours, then the driver may be advised to take rest. Further, the threshold value may vary in real-time based on health condition of drivers. For example, for a driver having a high sugar level or a high stress level, the threshold value may be set to 4 hours. The allocation of the vehicle is further based on route information (i.e., route conditions) of various routes. Thus, the method and the system of the disclosure ensure that the passenger 104 and the driver of the allocated vehicle do not traverse on routes that are polluted, or weather conditions associated with the routes affect the health conditions of the passenger 104 and/or the driver. Further, the method and the system of the disclosure includes selecting an optimum route based on the health conditions of the passenger 104 and the eligible drivers. Thus, the driver will not be considered if the route conditions may affect the health conditions of the driver. The allocation of the vehicle is further based on historical allocation information of the passenger 104 and/or the eligible drivers. This ensures that the unfit drivers are not repeatedly selected to offer rides to unfit passengers, or vice-versa. Thus, the method and the system of the present disclosure provide efficient, effective, and comprehensive way of allocating a vehicle to the passenger 104 as compared to a conventional method of vehicle allocation.

A person of ordinary skill in the art will appreciate that embodiments and exemplary scenarios of the disclosed subject matter may be practiced with various computer system configurations, including multi-core multiprocessor systems, minicomputers, mainframe computers, computers linked or clustered with distributed functions, as well as pervasive or miniature computers that may be embedded into virtually any device. Further, the operations may be described as a sequential process, however some of the operations may in fact be performed in parallel, concurrently, and/or in a distributed environment, and with program code stored locally or remotely for access by single or multiprocessor machines. In addition, in some embodiments, the order of operations may be rearranged without departing from the spirit of the disclosed subject matter.

Techniques consistent with the disclosure provide, among other features, systems and methods for allocating vehicles to passengers. While various exemplary embodiments of the disclosed allocating systems and methods have been described above, it should be understood that they have been presented for purposes of example only, and not limitations. It is not exhaustive and does not limit the disclosure to the precise form disclosed. Modifications and variations are possible in light of the above teachings or may be acquired from practicing of the disclosure, without departing from the breadth or scope.

While various embodiments of the disclosure have been illustrated and described, it will be clear that the disclosure is not limited to these embodiments only. Numerous modifications, changes, variations, substitutions, and equivalents will be apparent to those skilled in the art, without departing from the spirit and scope of the disclosure, as described in the claims.

What is claimed is:

1. A method, comprising:
  receiving, by circuitry, from a passenger device via a communication network, an online ride request of a passenger for a ride;
  obtaining, by the circuitry, based on the online ride request, real-time passenger fitness information of the passenger, by
    communicatively coupling with one or more first fitness accessories worn by the passenger and one or more first fitness applications running on the passenger device, wherein the one or more first fitness applications and the one or more first fitness accessories monitor real-time health conditions of the passenger using one or more fitness sensors to generate and record the real-time passenger fitness information, and accessing the real-time passenger fitness information recorded by the one or more first fitness applications and the one or more first fitness accessories;

determining, by the circuitry, whether the passenger is eligible for the ride based on passenger fitness information, including the obtained real-time passenger fitness information, of the passenger and the online ride request;

identifying, by the circuitry, a set of drivers available for offering the ride based on the online ride request and the determination that the passenger is eligible for the ride;

determining, by the circuitry, before vehicle allocation for the ride, a real-time driving pattern of each driver of the set of drivers based on on-board diagnostic data received from one or more sensors in a vehicle of each driver of the set of drivers;

selecting, by the circuitry, from the set of drivers, a subset of drivers based on the online ride request, driver fitness information of each driver of the set of drivers, and a logged-in time duration indicating a total time duration in a day for which each driver of the set of drivers has been driving a corresponding vehicle such that each driver in the subset of drivers is selected based on a corresponding logged-in time duration being less than a threshold value and a driver of the set of drivers is not selected in the subset of drivers based on a corresponding logged-in time duration being greater than the threshold value, wherein the driver fitness information of each driver of the set of drivers includes the determined real-time driving pattern;

selecting, by the circuitry, a first driver from the subset of drivers and a route from a set of routes associated with the online ride request, wherein the selection of the first driver and the route is based on the passenger fitness information, the driver fitness information of each driver of the subset of drivers, the logged-in time duration of each driver of the subset of drivers, the online ride request, and route information associated with each route of the set of routes;

allocating, by the circuitry, a first vehicle associated with the selected first driver to the passenger for the ride; and hosting, by the circuitry, on a driver device of the first driver, a digital map that displays the selected route and renders one or more directions to follow the selected route, wherein the first vehicle is driven along the selected route based on the hosted digital map.

2. The method of claim 1, wherein the online ride request includes at least one of a source location, a destination location, a vehicle type, or a ride type.

3. The method of claim 1, further comprising:
determining, by the circuitry, for the passenger, one or more passenger parameter values of one or more passenger physiological parameters, respectively, based on the passenger fitness information;

assigning, by the circuitry, a first severity rating to each passenger physiological parameter based on a degree of severity associated with each passenger parameter value; and determining, by the circuitry, a passenger fitness level of the passenger based on at least one of a passenger parameter value and the first severity rating associated with each of the one or more passenger physiological parameters, wherein the determination that whether the passenger is eligible for the ride is further based on the passenger fitness level and the one or more passenger parameter values.

4. The method of claim 1, further comprising:
determining, by the circuitry, for each driver, one or more driver parameter values of one or more driver physiological parameters, respectively, based on at least the driver fitness information and the logged-in time duration;

assigning, by the circuitry, a second severity rating to each driver physiological parameter based on a degree of severity associated with each driver parameter value; and determining, by the circuitry, a driver fitness level of each driver based on at least one of the driver parameter value and the second severity rating associated with each of the one or more driver physiological parameters, wherein a determination whether each driver of the subset of drivers is eligible for offering the ride is based on at least one of the driver fitness level and the one or more driver parameter values.

5. The method of claim 1, further comprising retrieving, by the circuitry from a database server, historical passenger fitness information of the passenger, wherein the passenger fitness information further includes the historical passenger fitness information of the passenger.

6. The method of claim 5, wherein the historical passenger fitness information includes historical health data and driver feedback data associated with the passenger, and wherein the historical health data associated with the passenger includes one or more health conditions of the passenger.

7. The method of claim 1, further comprising:
retrieving, by the circuitry from a database server, historical driver fitness information of each driver; and obtaining, by the circuitry, real-time driver fitness information of each driver of the set of drivers, by communicatively coupling with one or more fitness-monitoring devices installed in each vehicle of the set of drivers, one or more second fitness accessories worn by each driver of the set of drivers, one or more second fitness applications running on each driver device of each of the set of drivers, wherein the one or more fitness-monitoring devices, the one or more second fitness applications, and the one or more second fitness accessories monitor real-time health conditions of each driver of the set of drivers to generate and record the real-time passenger fitness information of each driver, and wherein the driver fitness information of each driver includes the historical driver fitness information and the real-time driver fitness information of each driver, and wherein the one or more fitness-monitoring devices includes an audio-recording device, an image-capturing device, an air quality detector, and an on-board diagnostic sensor (OBD) installed in each driver's vehicle, and accessing the real-time driver fitness information recorded by the one or more fitness-monitoring devices, the one or more second fitness applications, and the one or more second fitness accessories.

8. The method of claim 7, wherein the historical driver fitness information includes historical health data and passenger feedback data, and wherein the real-time driver fitness information received from the one or more fitness-monitoring devices indicates real-time health conditions of each driver.

9. The method of claim 1, wherein the route information associated with each route includes at least one of weather, road, pollution, geographical, or traffic conditions associated with each route.

10. The method of claim 1, wherein the first driver is further selected from the subset of drivers based on historical allocation information associated with the passenger and each driver of the subset of drivers.

11. The method of claim 1, further comprising:
retrieving, by the circuitry, from a database server, the route information of each of the set of routes connecting a source location and a destination location of the online ride request; and
rating, by the circuitry, each route of the set of routes based on the retrieved route information, wherein the selection of the route from the set of routes and the first driver is further based on the rating of each route.

12. The method of claim 1, further comprising:
hosting, by circuitry, on a passenger device of a passenger, a mobile application that provides vehicle services and supports a plurality of input modes, including two or more of: a touch-based input, a text-based input, a voice-based input, or a gesture-based input, of the passenger device, wherein the online ride request received by the circuitry includes a destination input provided based on at least one of the plurality of input modes supported by the mobile application on the passenger device.

13. A system, comprising:
circuitry configured to:
receive, from a passenger device of via a communication network, an online ride request of a passenger for a ride;
obtain, based on the online ride request, real-time passenger fitness information of the passenger, wherein to obtain the real-time passenger fitness information of the passenger, the circuitry is further configured to:
communicatively couple with one or more first fitness accessories worn by the passenger and one or more first fitness applications running on the passenger device, wherein the one or more first fitness applications and the one or more first fitness accessories monitor real-time health conditions of the passenger using one or more fitness sensors to generate and record the real-time passenger fitness information; and
access of the real-time passenger fitness information recorded by the one or more first fitness applications and the one or more first fitness accessories;
determine whether a passenger is eligible for the ride based on passenger fitness information, including the obtained real-time passenger fitness information, of the passenger and the online ride request;
identify a set of drivers available for offering the ride based on the online ride request and the determination that the passenger is eligible for the ride;
determine, before the ride is booked, a real-time driving pattern of each driver of the set of drivers based on on-board diagnostic data received from one or more sensors in a vehicle of each driver of the set of drivers;
select from the set of drivers, a subset of drivers based on the online ride request, driver fitness information of each driver of the set of drivers, and a logged-in time duration that indicates a total time duration in a day for which each driver has been driving a corresponding vehicle such that each driver in the subset of drivers is selected based on corresponding logged-in time duration being less than a threshold value and a driver of the set of drivers is not selected in the subset of drivers based on a corresponding logged-in time duration being greater than the threshold value, wherein the driver fitness information of each driver of the set of drivers includes the determined real-time driving pattern;
select a first driver from the subset of drivers and a route from a set of routes associated with the online ride request, wherein the first driver and the route are selected based on at least the passenger fitness information, the driver fitness information of each driver of the subset of drivers, the logged-in time duration of each driver of the subset of drivers, the online ride request, and route information associated with each route of the set of routes;
allocate a first vehicle associated with the selected first driver to the passenger for the ride; and
host, on a driver device of the first driver, a digital map that displays the selected route and renders one or more directions to follow the selected route, wherein the first vehicle is driven along the selected route based on the hosted digital map.

14. The system of claim 13, wherein the circuitry is further configured to:
determine, for the passenger, one or more passenger parameter values of one or more passenger physiological parameters, respectively, based on the passenger fitness information;
assign a first severity rating to each passenger physiological parameter based on a degree of severity associated with each passenger parameter value; and
determine a passenger fitness level of the passenger based on at least one of a passenger parameter value and the first severity rating associated with each of the one or more passenger physiological parameters, wherein the determination that whether the passenger is eligible for the ride is further based on the passenger fitness level and the one or more passenger parameter values.

15. The system of claim 13, wherein the circuitry is further configured to:
determine, for each driver, one or more driver parameter values of one or more driver physiological parameters, respectively, based on at least one of the driver fitness information and the logged-in time duration;
assign a second severity rating to each driver physiological parameter based on a degree of severity associated with each driver parameter value; and
determine a driver fitness level of each driver based on at least one of the driver parameter value and the second severity rating associated with each of the one or more driver physiological parameters, wherein a determination whether each driver of the subset of drivers is eligible for offering the ride is based on at least one of the driver fitness level and the one or more driver parameter values.

16. The system of claim 13, wherein the circuitry is further configured to retrieve historical passenger fitness information of the passenger from a database server, and wherein the passenger fitness information further includes the historical passenger fitness information of the passenger.

17. The system of claim 16, wherein the historical passenger fitness information includes historical health data and driver feedback data associated with the passenger, and wherein the historical health data associated with the passenger includes one or more health conditions of the passenger.

18. The system of claim 13, wherein the circuitry is further configured to:

retrieve, from a database server, historical driver fitness information of each driver; and obtain real-time driver fitness information of each driver of the set of drivers, wherein to obtain the real-time driver fitness information of each driver, the circuitry is further configured to:
communicatively couple with one or more fitness-monitoring devices installed in each vehicle of the set of drivers, one or more second fitness accessories worn by each driver of the set of drivers, one or more second fitness applications running on each driver device of each of the set of drivers, wherein the one or more fitness-monitoring devices, the one or more second fitness applications, and the one or more second fitness accessories monitor real-time health conditions of each driver of the set of drivers to generate and record the real-time passenger fitness information of each driver, wherein the driver fitness information includes the historical driver fitness information and the real-time driver fitness information of each driver, and wherein the one or more fitness-monitoring devices includes an audio-recording device, an image-capturing device, an air quality detector, and an on-board diagnostic sensor (OBD) installed in each driver's vehicle, and
access the real-time driver fitness information recorded by the one or more second fitness applications and the one or more second fitness accessories.

19. The system of claim 18, wherein the historical driver fitness information includes historical health data and passenger feedback data, and wherein the real-time driver fitness information received from the one or more fitness-monitoring devices indicates real-time health conditions of each driver.

20. The system of claim 13, wherein the first driver is further selected from the subset of drivers based on historical allocation information associated with the passenger and each driver of the subset of drivers.

* * * * *